US009814810B2

United States Patent
Cucin

(10) Patent No.: US 9,814,810 B2
(45) Date of Patent: *Nov. 14, 2017

(54) TISSUE SAMPLING, COLLECTION, AND PROCESSING SYSTEM

(75) Inventor: Robert L. Cucin, West Palm Beach, FL (US)

(73) Assignee: ROCIN LABORATORIES, INC., West Palm Beach, FL (US)

( * ) Notice: Subject to any disclaimer, the term of this patent is extended or adjusted under 35 U.S.C. 154(b) by 851 days.

This patent is subject to a terminal disclaimer.

(21) Appl. No.: 13/315,243

(22) Filed: Dec. 8, 2011

(65) Prior Publication Data

US 2012/0150069 A1 Jun. 14, 2012

Related U.S. Application Data

(63) Continuation of application No. 12/955,420, filed on Nov. 29, 2010, now abandoned, which is a continuation-in-part of application No. 12/850,786, filed on Aug. 5, 2010, now Pat. No. 8,465,471, which is a continuation-in-part of application No. 12/462,596, filed on Aug. 5, 2009, now Pat. No. 8,348,929, and a continuation-in-part of application No. 12/813,067, filed on Jun. 10, 2010, now abandoned.

(51) Int. Cl.
| | |
|---|---|
| *A61M 1/00* | (2006.01) |
| *A61B 10/02* | (2006.01) |
| *A61M 27/00* | (2006.01) |
| *A61B 19/00* | (2006.01) |
| *A61B 18/04* | (2006.01) |

(52) U.S. Cl.
CPC ........... *A61M 1/0058* (2013.01); *A61B 10/02* (2013.01); *A61B 10/0283* (2013.01)

(58) Field of Classification Search
CPC ......... A61M 1/00; A61M 27/00; A61B 19/00; A61B 18/04; A61F 5/00; A61F 17/43
USPC .... 604/313, 319, 403, 540–544; 606/32, 40; 600/109, 110, 425; 211/41.1, 41.7, 60.1, 211/85.13
See application file for complete search history.

(56) References Cited

U.S. PATENT DOCUMENTS

| | | | |
|---|---|---|---|
| 2,768,754 | A | 10/1956 | Briggs |
| 2,895,162 | A | 7/1959 | Harris |
| 3,938,505 | A | 2/1976 | Jamshidi |
| 4,083,706 | A | 4/1978 | Wiley |
| 4,568,332 | A | 2/1986 | Shippert |
| 4,651,753 | A | 3/1987 | Lifton |
| 4,710,162 | A | 12/1987 | Johnson |
| 4,744,789 | A | 5/1988 | Johnson |
| 4,834,703 | A | 5/1989 | Dubrul et al. |
| 4,886,492 | A | 12/1989 | Brooke |

(Continued)

FOREIGN PATENT DOCUMENTS

WO 2011017517 A 2/2011

*Primary Examiner* — Tatyana Zalukaeva
*Assistant Examiner* — Ilya Treyger
(74) *Attorney, Agent, or Firm* — Thomas J. Perkowski, Esq., PC

(57) ABSTRACT

A tissue sampling, collection, and processing system including a hand-supportable power-assisted tissue aspiration device having a cannula for aspirating fat tissue from a patient's body, and a multi-pack tissue sampling, processing and collecting device, installed between the tissue aspiration device and a vacuum source, and containing multiple tissue collection tubes for collection of aspirated fat tissue samples.

14 Claims, 57 Drawing Sheets

(56) References Cited

U.S. PATENT DOCUMENTS

| | | |
|---|---|---|
| 5,027,827 A | 7/1991 | Cody |
| 5,052,999 A | 10/1991 | Klein |
| 5,102,410 A | 4/1992 | Dressel |
| 5,112,302 A | 5/1992 | Cucin |
| 5,348,022 A | 9/1994 | Leigh et al. |
| 5,348,535 A | 9/1994 | Cucin |
| 5,358,638 A | 10/1994 | Gershenson |
| 5,372,945 A | 12/1994 | Alchas et al. |
| 5,643,198 A | 7/1997 | Cucin |
| 5,865,803 A | 2/1999 | Major |
| 6,162,187 A | 12/2000 | Buzzard et al. |
| 6,190,364 B1 | 2/2001 | Imbert |
| 6,316,247 B1 | 11/2001 | Katz et al. |
| 6,346,107 B1 | 2/2002 | Cucin |
| 6,394,973 B1 | 5/2002 | Cucin |
| 6,468,225 B1 | 10/2002 | Lundgren |
| 6,471,069 B2 | 10/2002 | Lin et al. |
| 6,520,935 B1 | 2/2003 | Jansen et al. |
| 6,544,211 B1 | 4/2003 | Andrew et al. |
| 6,544,246 B1 | 4/2003 | Niedospial, Jr. |
| 6,554,803 B1 | 4/2003 | Ashman |
| 6,632,182 B1 | 10/2003 | Treat |
| 6,638,235 B2 | 10/2003 | Miller et al. |
| 6,652,522 B2 | 11/2003 | Cucin |
| 6,676,629 B2 | 1/2004 | Andrew et al. |
| 6,761,701 B2 | 7/2004 | Cucin |
| 6,795,728 B2 | 9/2004 | Chornenky et al. |
| 6,872,199 B2 | 3/2005 | Cucin |
| 6,951,611 B2 | 10/2005 | Dannenmaier et al. |
| 7,041,217 B1 | 5/2006 | Close et al. |
| 7,306,740 B2 | 12/2007 | Freund |
| 7,381,206 B2 | 6/2008 | Cucin |
| 7,384,417 B2 | 6/2008 | Cucin |
| 7,390,484 B2 | 6/2008 | Fraser et al. |
| 7,473,420 B2 | 1/2009 | Fraser et al. |
| 7,488,427 B2 | 2/2009 | Freund |
| 7,501,115 B2 | 3/2009 | Fraser et al. |
| 7,514,075 B2 | 4/2009 | Hedrick et al. |
| 7,595,043 B2 | 9/2009 | Hedrick et al. |
| 7,651,684 B2 | 1/2010 | Hedrick et al. |
| 7,687,059 B2 | 3/2010 | Fraser et al. |
| 7,740,605 B2 | 6/2010 | Cucin |
| 7,771,716 B2 | 8/2010 | Hedrick et al. |
| 7,780,649 B2 | 8/2010 | Shippert |
| 7,789,872 B2 | 9/2010 | Shippert |
| 7,794,449 B2 | 9/2010 | Shippert |
| 7,887,795 B2 | 2/2011 | Fraser et al. |
| 7,901,672 B2 | 3/2011 | Fraser et al. |
| 8,062,286 B2 | 11/2011 | Shippert |
| 8,105,580 B2 | 1/2012 | Fraser et al. |
| 8,119,121 B2 | 2/2012 | Fraser et al. |
| 8,133,389 B2 | 3/2012 | Dorian et al. |
| 8,152,821 B2 | 4/2012 | Gambale et al. |
| 8,182,450 B2 | 5/2012 | Moosheimer et al. |
| 2001/0014785 A1 | 8/2001 | Sussman et al. |
| 2002/0138047 A1 | 9/2002 | Lopez |
| 2002/0151874 A1 | 10/2002 | Kolster et al. |
| 2004/0222137 A1 | 11/2004 | Hashimoto |
| 2005/0049521 A1 | 3/2005 | Miller et al. |
| 2007/0239176 A1 | 10/2007 | Stokes et al. |
| 2009/0192498 A1 | 7/2009 | Andrew et al. |

Components of the Tissue Sampling, Processing and Injection Syringe Device of the Present Invention
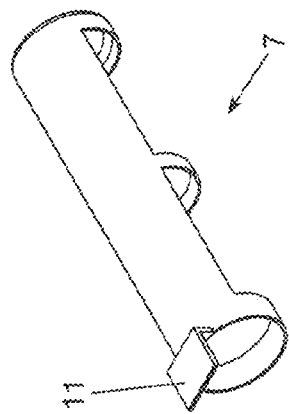
FIG. 2A1
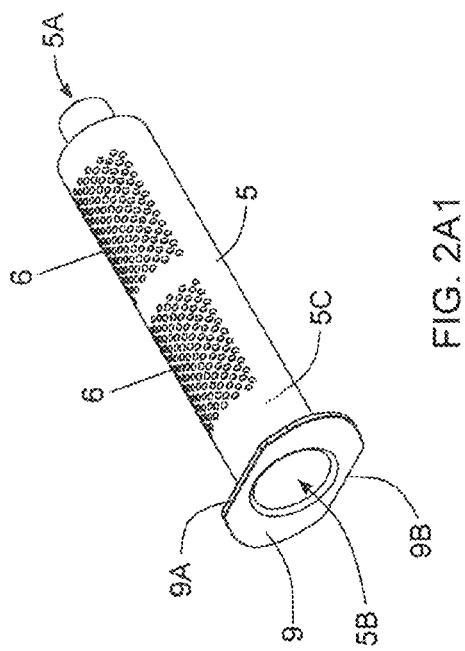
FIG. 2A3
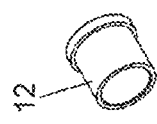
FIG. 2A2
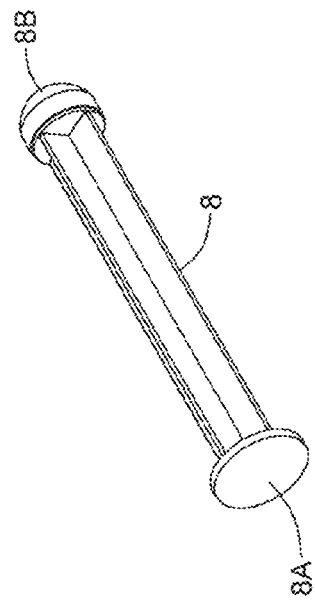
FIG. 2A4

Method of Harvesting Tissue Sample from a Patient using the Tissue Sampling, Processing and Injection Syringe Device of the Present Invention

- STEP 1. Remove tip cap from the Syringe Device.
- STEP 2. Occlude micro-pores on the Syringe Device.
- STEP 3. Attach suitable cannula to Syringe Device, and then insert cannula into donor site of patient.
- STEP 4. Withdraw plunger to create vacuum and collect fat in Syringe Device, until full.
- STEP 5 (optional): Aspirate a volume of irrigation solution through the Syringe Device, containing a collection tissue sample, to lavage the sample after harvesting.
- STEP 6. Remove cannula from patient.
- STEP 7. Cap tip of the Syringe Device.

FIG. 5

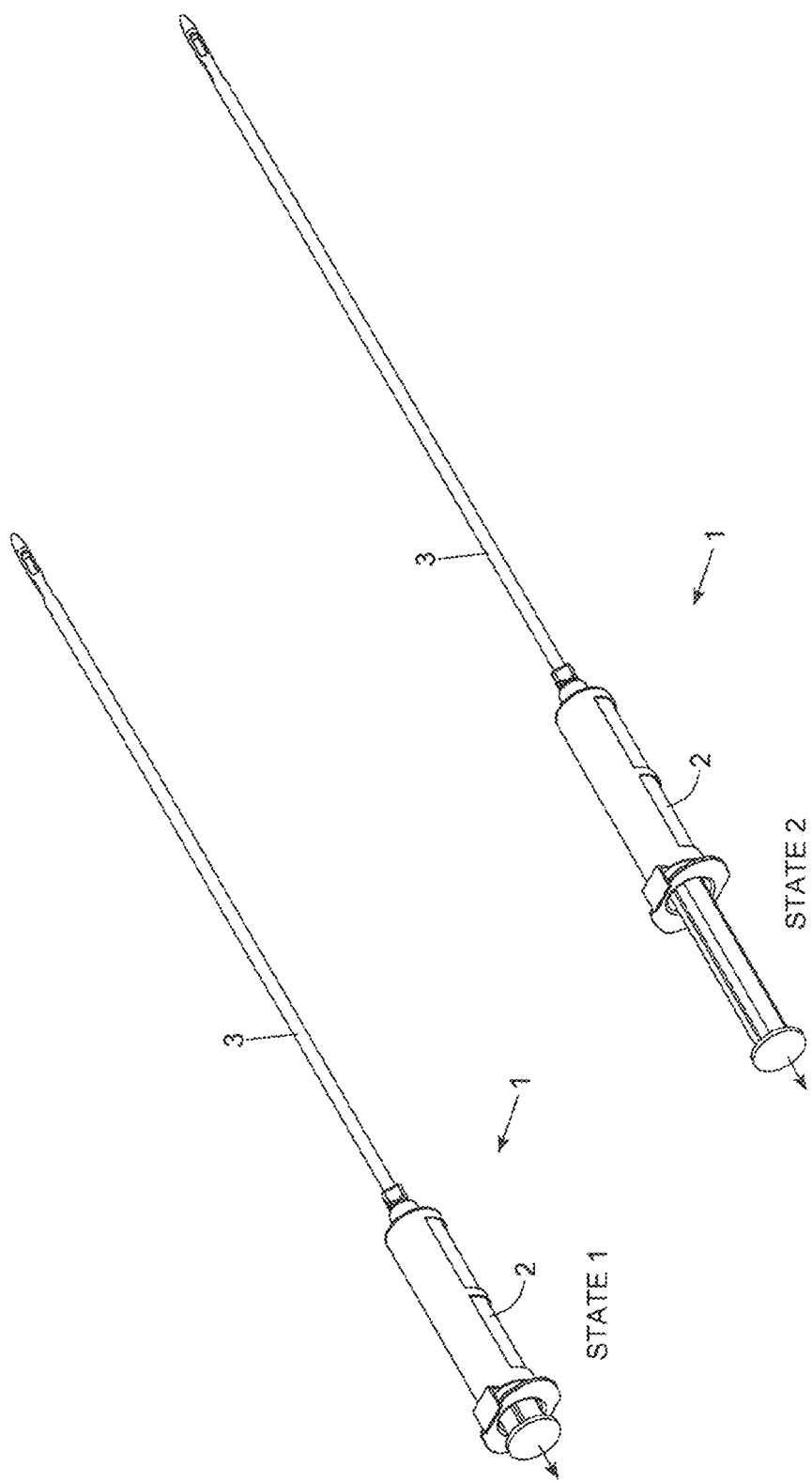

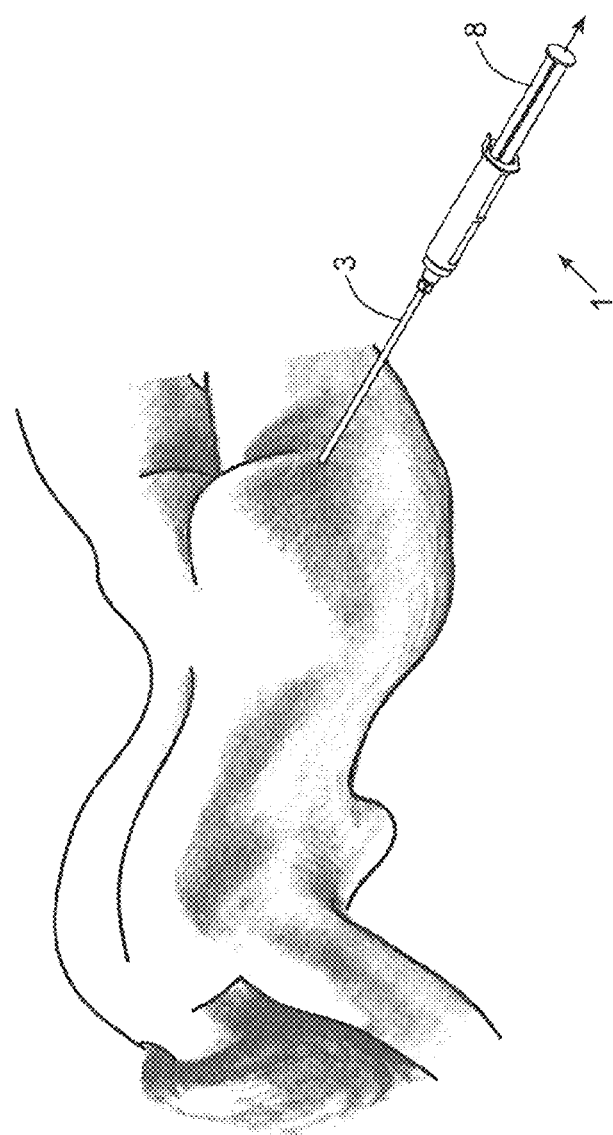

Method of Processing Aspirated Tissue Sample using the Tissue Sampling, Processing and Injection Syringe Device of the Present Invention

- STEP 1. Removing Cannula and Removing Cap tip (or cover with finger, the tip of the Syringe Device.
- STEP 2. Expose micro-pores of the Syringe.
- STEP 3. Gently depress plunger to express extra fluid.
- STEP 4. Cover micro-pores on Syringe Device now containing a collected sample of concentrated fat tissue.

FIG. 6

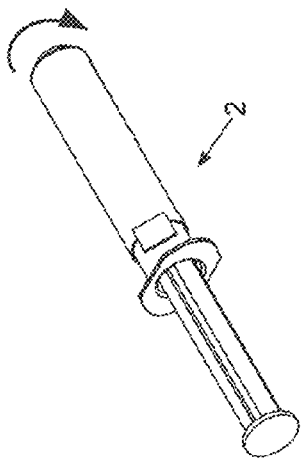
FIG. 6B3
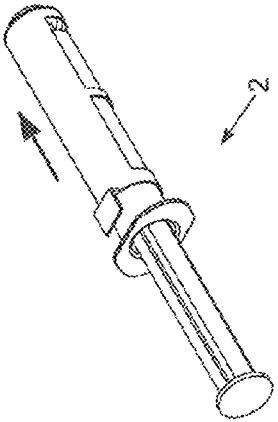
FIG. 6B2
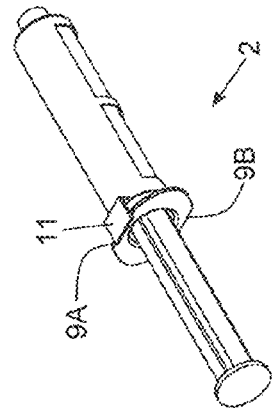
FIG. 6B1
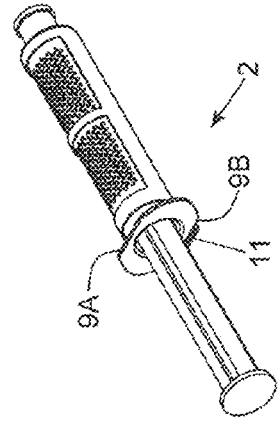
FIG. 6B6
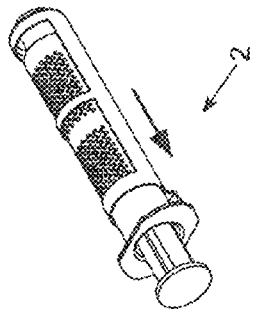
FIG. 6B5
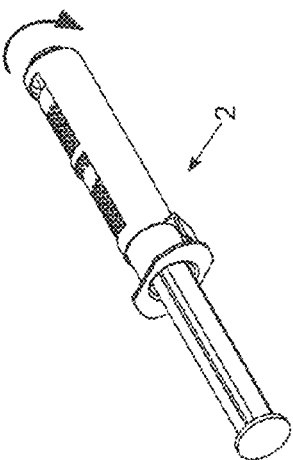
FIG. 6B4

Method of Injecting Processed Tissue in a Patient using the Tissue Sampling, Processing and Injection Syringe Device of the Present Invention

- STEP 1. Remove tip cover of the Syringe Device.
- STEP 2. Cover micro-pores on syringe with occluder.
- STEP 3. Attach cannula and insert where correction is required, by depressing plunger to inject fat as required.
- STEP 4 (Optional). Eject tissue sample material out of the Syringe Device into an empty (no air) plastic bag for the purpose of delivering tissue material to skin bank.

FIG. 7

| PROCEDURE | SINGLE SYRINGE |
|---|---|
| Harvest | 1. Remove tip cap. |
| | 2. Attach cannula. |
| | 3. Occlude holes. |
| | 4. Withdraw plunger to create vacuum and collect fat in syringe until full. |
| Process | 1. Cap tip or cover tip with finger. |
| | 2. Expose holes. |
| | 3. Gently depress plunger to express extra fluid. |
| | 4. Cover holes on syringe now containing concentrated fat. |
| Inject | 1. Remove tip cover. |
| | 2. Cover holes on syringe with occluder. |
| | 3. Attach cannula and insert where correction is required. |
| | 4. Depress plunger to inject fat as required. |

FIG. 8

Method of Harvesting Tissue Samples from a Patient using the 3-Pack Tissue Sampling, Processing and Collection Device of the Present Invention, Connected In-Line with Hand-Held Tissue Aspiration Instrument

- STEP 1. Unscrew barb on back of hand-held tissue aspiration instrument.
- STEP 2. Screw on the 3-Pack Tissue Sampling, Processing and Collection Device to hand piece of a powered tissue aspiration instrument.
- STEP 3. Attach back barb of 3-pack Tissue Sampling, Processing and Collection Device to vacuum.
- STEP 4. Tumesce the selected area with irrigation fluid during tissue aspiration, if desired.
- STEP 5. Aspirate fat tissue until 3 tissue collection syringes within the Device are filled with fat tissue.
- STEP 6 (optional). Aspirate a volume of irrigation solution to lavage the tissue samples after sampling and collection within the Device.

FIG. 9

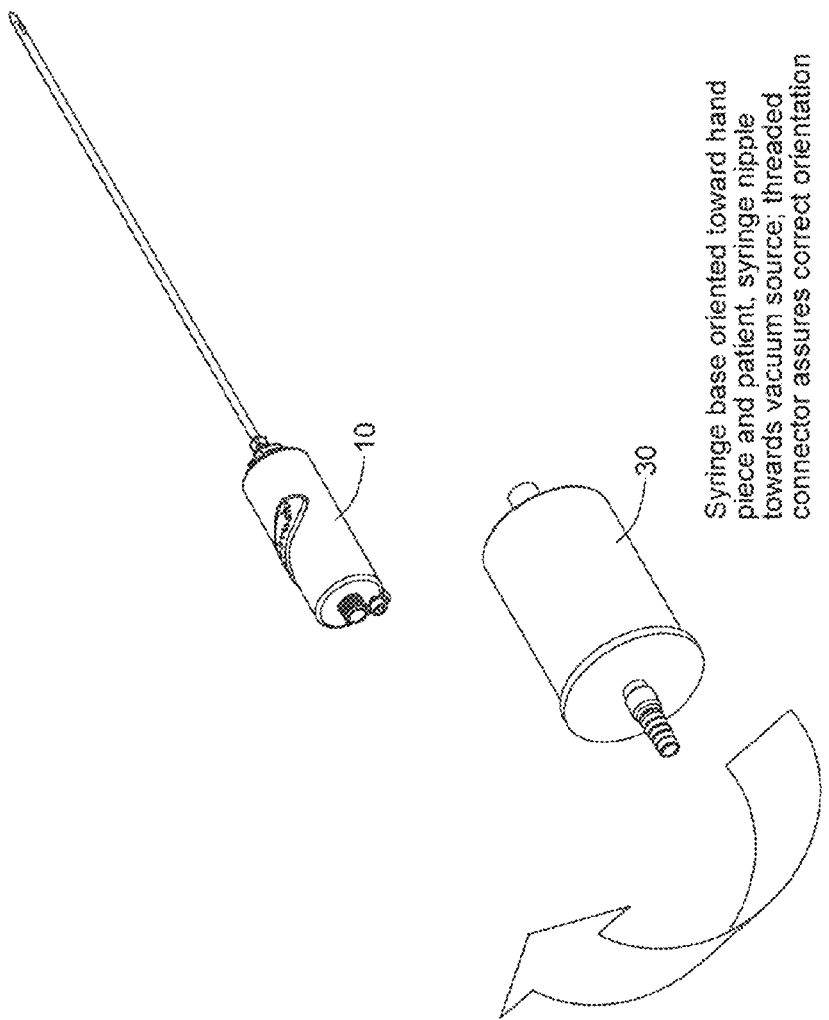

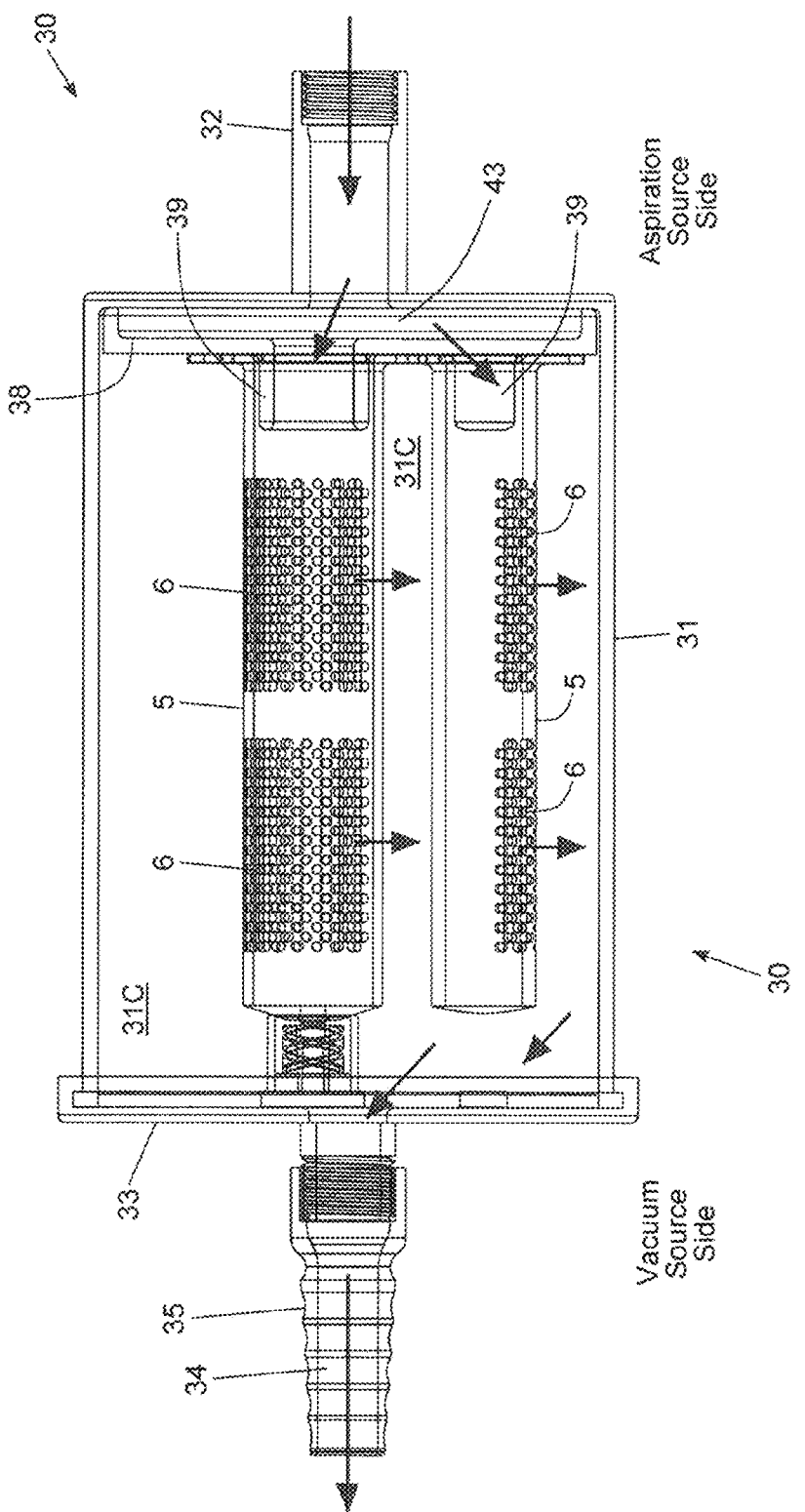

Method of Processing Aspirated Tissue During Harvesting using 3-Pack Tissue Sampling, Processing and Collection Device Coupled In-Line with Hand-Held Tissue Aspiration Instrument

- STEP 1. Tissue processing, filtration and concentration operations occurs automatically during aspiration and collection operations.
- STEP 2. Remove vacuum tubing from the 3-Pack Device.
- STEP 3. Unscrew the 3-Pack Device from the hand piece of the tissue aspiration instrument.
- STEP 4. Replace the barbed connector on back of the hand piece of the instrument.
- STEP 5. Remove the lid from the 3-Pack Device.
- STEP 6. Remove the fat-filled capped tissue collection tubes from the suction plate of the 3-Pack Device, attach a cap to the distal end opening of each fat-filled tissue collection tube, and then face the capped collection tubes downwardly.
- STEP 7. Insert a plunger and piston subassembly into the proximal end opening of each capped tissue collection tube, and deliver the capped tissue collection tubes to the surgeon, for immediate reinjection into the patient.
- STEP 7 (Optionally). Deliver the collection tubes, plunger up, to a skin banking facility, where a musculoskeletal stem cell line or hematopoietic line can be grown out to recoup a stem cell enriched culture of cells that may be returned to the surgeon for auto-graft into the patient, with adipose cell markers, ideal for facial rejuvenation.

FIG. 10

Method of Injecting Processed Tissue Samples into a Patient using a Fat-Filled Tissue Injection Syringe Device of Present Invention

- STEP 1. Remove the distal tip cap from the fat-filled tissue collection tube.
- STEP 2. Slide on a micro-pore occluder over the tissue collection tube so as to cover the micro-pores, and snap the flange in place with the micro-pore occluder, to form a tissue injection syringe device.
- STEP 3. Screw on a luer lock cannula to the distal tip portion of the tissue injection syringe device for reinjection of harvested and processed tissue sample.
- STEP 4. Insert the cannula into area of correction.
- STEP 5. Gently depress plunger's piston to inject sufficient tissue into the patient to obtain the desired correction.

FIG. 11

| PROCEDURE | | 3-PACK |
|---|---|---|
| Harvest | | 1. Unscrew barb on back of Airbrush IIIE hand piece. |
| | | 2. Screw on 3-pack assembly to hand piece. Note correct orientation. |
| | | 3. Attach back barb of 3-pack collection assembly to vacuum. |
| | | 4. Tumesce selected area for aspiration if desired. |
| | | 5. Aspirate fat until 3 syringes are filled with fat. |
| Process | | 1. Processing happens during aspiration. |
| | | 2. Remove vacuum tubing from 3-pack collection assembly. |
| | | 3. Unscrew collection assembly from hand piece. |
| | | 4. Replace barb on back of hand piece. |
| | | 5. Remove lid from collector assembly. |
| | | 6. Remove fat-filled syringes from collection assembly, tip down. |
| Inject | | 1. Remove tip cap. |
| | | 2. Slide on occluder to cover holes and snap over syringe flange. |
| | | 3. Screw on any luer lock cannula for reinjection. |
| | | 4. Insert cannula into area of correction. |
| | | 5. Gently depress plunger to inject sufficient to obtain desired correction. |

FIG. 12

Method of Sampling Aspirated Tissue Samples using 6-Pack Tissue Sampling, Processing and Collection Device of the Present Invention, Allowing the Surgeon to Select which Collection Tubes to Fill at any Given Moment, While Coupled In-Line with a Hand-Held Tissue Aspiration Instrument

- STEP 1. Insert 6-pack Tissue Sampling, Processing and Collection Device between cannula or hand piece and vacuum source.
- STEP 2. Tumesce the aspiration area as desired.
- STEP 3. Aspirate fat until 6 collection syringes are filled with fat tissue.
- STEP 4 (optional). Aspirate a volume of irrigation solution to lavage the samples in the syringe collection tubes, after harvesting, processing and collection.

FIG. 13

In-Line Serial Six-Pack Tissue Sampling, Processing and Collection Device of the Present Invention

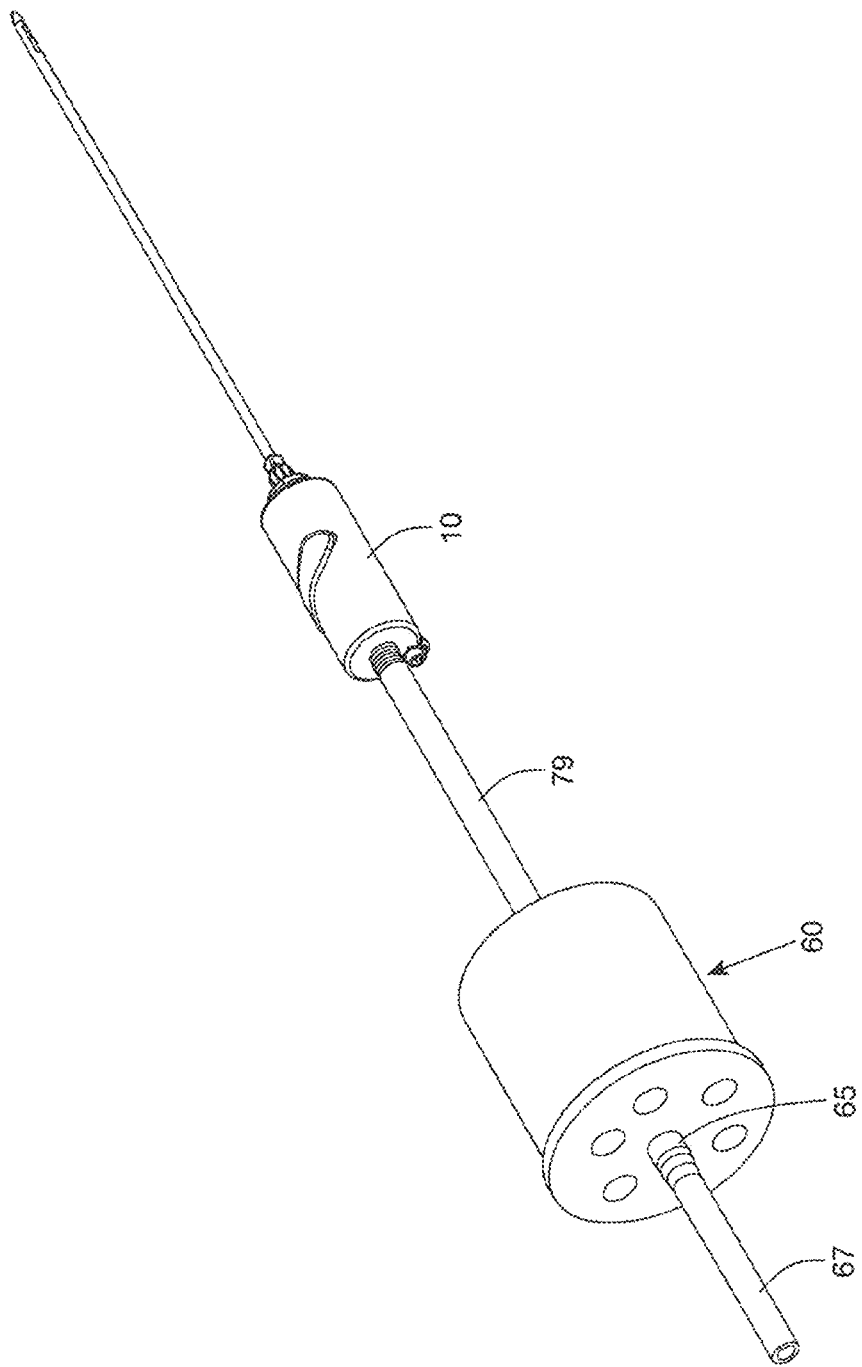

Method of Processing Aspirated Tissue During Harvesting Using the Six-Pack Tissue Sampling, Processing and Collection Device of the Present Invention

- STEP 1. Tissue processing, filtration and concentration operations occurs automatically during aspiration and collection operations.
- STEP 2. Remove vacuum tubing from the 3-Pack Device.
- STEP 3. Unscrew the 3-Pack Device from the hand piece of the tissue aspiration instrument.
- STEP 4. Replace the barbed connector on back of the hand piece of the instrument.
- STEP 5. Remove the lid from the 3-Pack Device.
- STEP 6. Remove the fat-filled capped tissue collection tubes from the suction plate of the 3-Pack Device, attach a cap to the distal end opening of each fat-filled tissue collection tube, and then face the capped collection tubes downwardly.
- STEP 7. Insert a plunger and piston subassembly into the proximal end opening of each capped tissue collection tube, and deliver the capped tissue collection tubes to the surgeon, for immediate reinjection into the patient.
- STEP 7 (Optionally). Deliver the collection tubes, plunger up, to a skin banking facility, where a musculoskeletal stem cell line or hematopoietic line can be grown out to recoup a stem cell enriched culture of cells that may be returned to the surgeon for auto-graft into the patient, with adipose cell markers, ideal for facial rejuvenation.

FIG. 14

Method of Injecting Processed Tissue Samples into a Patient Using a Fat-Filled Tissue Injection Syringe Device of Present Invention

- STEP 1. Remove the distal tip cap from the fat-filled tissue collection tube.
- STEP 2. Slide on a micro-pore occluder over the tissue collection tube so as to cover the micro-pores, and snap the flange in place with the micro-pore occluder, to form a tissue injection syringe device.
- STEP 3. Screw on a luer lock cannula to the distal tip portion of the tissue injection syringe device for reinjection of harvested and processed tissue sample.
- STEP 4. Insert the cannula into area of correction.
- STEP 5. Gently depress plunger's piston to inject sufficient tissue into the patient to obtain the desired correction.

FIG. 15

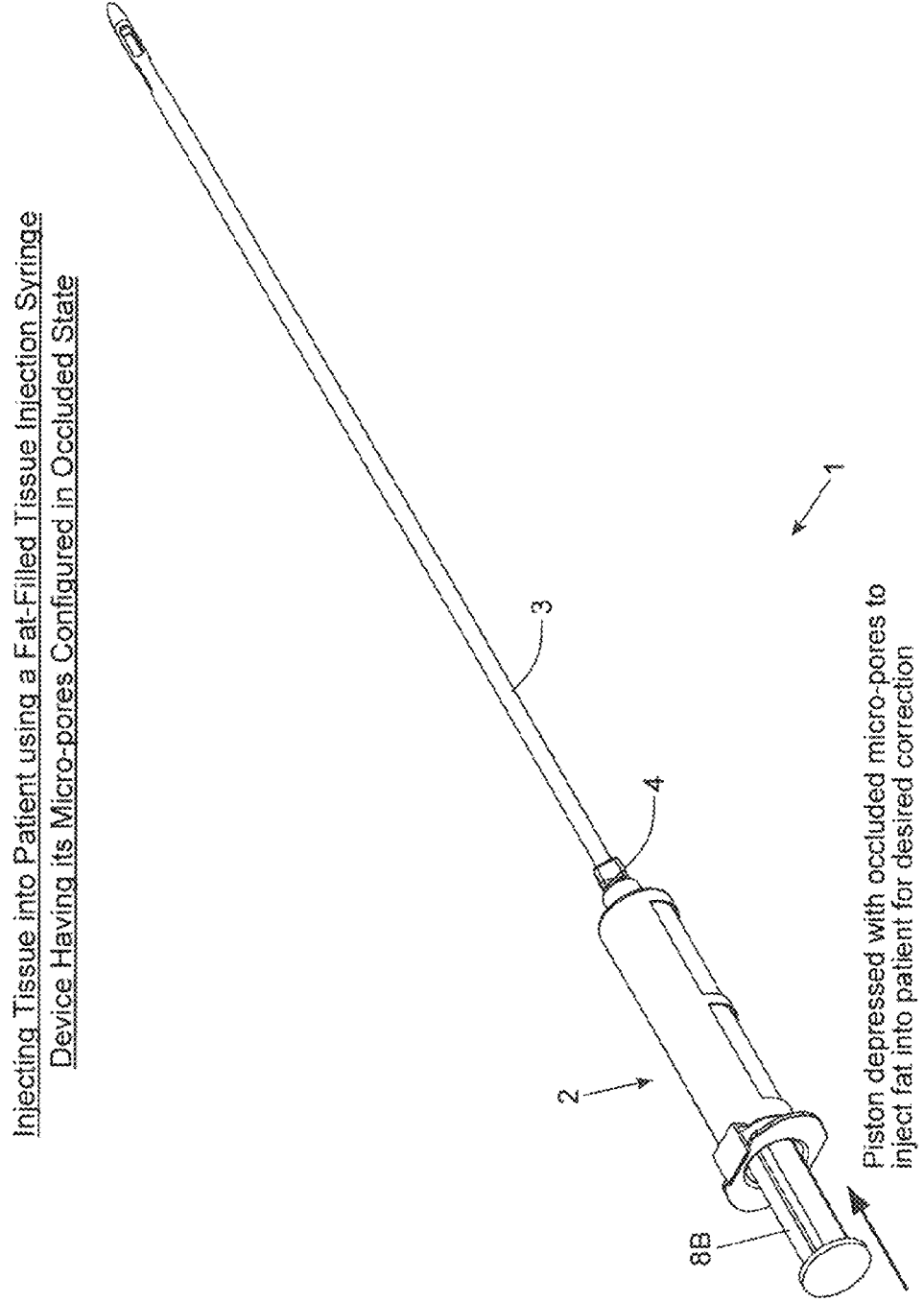

| PROCEDURE | 6-Pack | |
|---|---|---|
| Harvest | 1. Interpolate 6-pack collector between cannula or hand piece and vacuum source. | |
| | 2. Tumesce aspiration area as desired. | |
| | 3. Aspirate fat until 6 syringes are filled with fat. | |
| Process | 1. Processing happens during aspiration. | |
| | 2. Remove vacuum tubing from 6-pack collection assembly. | |
| | 3. Remove lid from collector assembly. | |
| | 4. Remove fat-filled syringes from collection assembly, tip down. | |
| Inject | 1. Remove tip cap. | |
| | 3. Slide on occluder to cover holes and snap over syringe flange. | |
| | 3. Screw on any luer lock cannula for reinjection. | |
| | 4. Insert cannula into area of correction. | |
| | 5. Gently depress plunger to inject sufficient to obtain desired correction. | |

FIG. 16

TISSUE SAMPLING, COLLECTION, AND PROCESSING SYSTEM

RELATED CASES

This application is a Continuation of application Ser. No. 12/955,420 filed Nov. 29, 2010 now abandoned; which is a Continuation-in-Part (CIP) of application Ser. No. 12/850,786 filed on Aug. 5, 2010 now U.S. Pat. No. 8,465,471, which is a CIP of application Ser. No. 12/462,596 filed Aug. 5, 2009 now U.S. Pat. No. 8,348,929, and copending application Ser. No. 12/813,067 filed Jun. 10, 2010 now abandoned; wherein each said Application is owned by Rocin Laboratories, Inc., and incorporated herein by reference in its entirety.

BACKGROUND OF THE INVENTION

Field of the Invention

The present invention relates to improvements in methods of and apparatus for sampling, processing and collecting tissue samples using aspiration processes.

Brief Description of the State of Knowledge in the Art

There are many applications where human tissue is harvested, processed and transplanted back into human beings for various cosmetic, reconstructive and biomedical reasons.

In general, there are various types of human tissue involved in such transplantation procedures, including autologous and allogeneic forms of adipose (i.e. fat) and musculoskeletal (i.e. bone, ligament, cartilage and skin) tissue, for use in autografting and allografting.

Also, in recent times, public confidence in and comfort with synthetic materials (e.g., silicone and teflon) and foreign tissues (e.g., bovine collagen) has declined. Conversely, the interest in and demand for autologous adipose tissue transplantation has risen.

Typically, autologous adipose tissue transplantation involves the procurement of adipose tissue by liposuction techniques from an area of abundance, and re-injection of the harvested adipose tissue into a different site of the same individual for cosmetic/reconstructive augmentation or enhancement purposes.

Generally, adipose tissue must be as 'clean' or refined as possible before re-introduction to maximize the chances of graft survival. Such refinement preferably is done with as little exposure of the tissue to air as possible (i.e., "anaerobic tissue handling").

Unfortunately, the nature of conventional liposuction procedures have precluded easy tissue isolation after initial harvest (especially on a large scale) because the volume and/or viscosity of 'raw' liposuction effluent also contains unwanted components, e.g., oil, blood and anesthetic solution.

Currently, there are no standard techniques, methods, or devices that exist for the simple, large scale isolation and refinement of liposuction-harvested adipose tissue. Although cannulas, needles and methods for tissue harvest and preparation exist, these techniques are tedious, inefficient and require a pseudo-sterile centrifugation step.

Several devices exist for the isolation of certain cells.

For example, U.S. Pat. Nos. 5,035,708 and 5,372,945, issued to Alchas et al., describe an endothelial cell procurement and deposition kit and a device and method for collecting and processing fat tissue and procuring microvessel endothelial cells to produce endothelial cell products.

U.S. Pat. No. 6,316,247 to Katz et al discloses a method of and apparatus for separating adipose tissue for autologous tissue transplantation. Liposuctioned tissue removed from the patient is transferred into the device through the inlet port that is contiguous with the inner flexible porous container. Pieces of adipose tissue are "trapped" within the inner flexible container whereas waste components (free oil, blood, serum) are able to drain through the pores and out the outlet port. After all the desired liposuction effluent is transferred, the trapped tissue may be rinsed thoroughly with saline or buffer. For very thorough cleansing, the outlet port is sealed, buffer is added, and the inlet port is sealed. The device is agitated to encourage thorough rinsing of the tissue, and then the device is held upright and the bottom outlet port unsealed to allow for drainage of waste or active suction of the effluent. This step can be repeated several times as necessary to achieve tissue that is highly "purified". Finally, the washed tissue can be expressed from the inner flexible container by 'rolling' the tissue out through the inlet port (from bottom to top) into receptacles, e.g., syringes, for re-implantation or any other desired receptacle for further preparation before injection. Alternatively, a receptacle can be attached directly to the port such that the tissue can be anaerobically re-injected into the body.

While U.S. Pat. No. 6,316,247 to Katz et al discloses an improved device for harvesting and processing fat tissue during liposuction operations, it involves complex tissue cleansing operations, and handling operations which make it either impractical or undesirable in surgical environments.

Thus, there is a great need in the art for a new and improved method of and apparatus for safely harvesting, processing (i.e. preparing) and collecting adipose and other forms of tissue for immediate autologous tissue transplantation, explant culture endeavors or cell dissociations, while avoiding the shortcomings and drawbacks of the prior art methods and apparatus.

OBJECTS AND SUMMARY OF THE PRESENT INVENTION

Accordingly, it is a primary object of the present invention to provide a new and improved method of and apparatus for safely harvesting, processing (i.e. preparing) and collecting adipose and other forms of tissue for immediate autologous tissue transplantation, explant culture endeavors or cell dissociations, while avoiding the shortcomings and drawbacks of the prior art methods and apparatus.

Another object of the present invention is to provide a new tissue sampling, processing and injection syringe device which avoids the shortcomings and drawbacks of the prior art apparatus and methodologies.

Another object of the present invention is to provide an improved method of harvesting a tissue sample from a patient or donor using the tissue sampling, processing and injection syringe device.

Another object of the present invention is to provide an improved method of processing aspirated tissue sample using the tissue sampling, processing and injection syringe device. Another object of the present invention is to provide an improved method of injecting a processed tissue sample into a patient using a filled tissue sampling, processing and injection syringe.

Another object of the present invention is to provide an improved method of harvesting, processing and injecting a tissue sample into a patient using the tissue sampling, processing and injection syringe device.

Another object of the present invention is to provide an improved in-line three-pack tissue sampling, processing and collection device.

Another object of the present invention is to provide an improved method of processing aspirated tissue during harvesting using the 3-pack tissue sampling, processing and collection device of the present invention, coupled in-line to a hand-held powered tissue aspiration instrument.

Another object of the present invention is to provide an improved method of injecting processed tissue samples into a patient using a fat-filled tissue injection syringe device.

Another object of the present invention is to provide an improved method of harvesting, processing and injecting a tissue sample into a patient using the tissue sampling, processing and injection syringe device.

Another object of the present invention is to provide an improved in-line six-pack tissue sampling, processing and collection device.

Another object of the present invention is to provide an improved method of processing aspirated tissue during harvesting using the six-pack tissue sampling, processing and collection device Another object of the present invention is to provide an improved method of injecting processed tissue into a patient using a fat-filled tissue injection syringe device.

Another object of the present invention is to provide an improved method of harvesting, processing and injecting a tissue sample into a patient using the tissue sampling, processing and injection syringe device.

Another object of the present invention is to provide improved tissue sampling, processing and collection devices which can be designed for single-use, as sterile consumables with a high profit margin.

Another object of the present invention is to provide improved tissue sampling, processing and collection devices which can be easily integrated with stem cell storage banks and cellular differentiation and enrichment programs.

Another object of the present invention is to provide improved tissue sampling, processing and collection devices which obviate the need for decanting, tissue transfers, autoclaving, or straining operations.

Another object of the present invention is to provide improved tissue sampling, processing and collection devices which enable gentle tissue harvesting operations, without heat, tissue trauma, blood loss, or surgeon effort.

Another object of the present invention is to provide a tissue sampling, collection, processing and re-injection system employing the modular and disposable tissue collection components which can be used in both manually-powered and vacuum-powered tissue sampling, processing and collection systems, providing significant levels of improvement in flexibility, convenience, and economy.

Another object of the present invention is to provide improved tissue sampling, processing and collection methods which work with both integrated and independent single-use sterile devices for aspirating, collecting, selectively sampling, processing, and re-injecting tissue.

Another object of the present invention is to provide such tissue sampling, processing and collection methods which can be practiced using low vacuum aspiration pressures, to minimize cellular rupture and oils.

Another object of the present invention is to provide improved tissue sampling, processing and collection methods, wherein aspirated and collected fat tissue is gently cleaned by tumescent fluid used during tissue aspiration operations, and wherein fluids and oils within tissue aspirants filtered through non-occluded micro-pores formed in tissue collection tubes employed in the apparatus.

Another object of the present invention is to provide improved tissue sampling, processing and collection methods which lavage harvested fat cells within the tissue collection apparatus of the present invention, along with an insulin or a growth factor enriched solution aspirated during tissue aspiration operations.

Another object of the present invention is to provide improved tissue sampling, processing and collection methods which result in lower cellular injury leading to higher graft survival rates.

Another object of the present invention is to provide improved tissue sampling, processing and collection methods, wherein collected tissue autografts can be stored for up to two years in an ordinary freezer (2-3° F.) without requiring cryopreservation.

Another object of the present invention is to provide improved tissue sampling, processing and collection platform which provides an autograft concentrate for an integrated banking program with optional further processing of adipocytes and stem cells.

Another object of the present invention is to provide improved tissue sampling, processing and collection methods which can be used for treating: facial wrinkles; scars and over-treated areas; Romberg's hemifacial atrophy; AIDS wasting; microsomia; facial revoluminization and youthfulization; breast augmentation; breast reconstruction; butt augmentation; and calf augmentation.

Another object of the present invention is to provide improved tissue sampling, processing and collection methods which minimize allergy or rejection from autograft.

Another object of the present invention is to provide improved tissue sampling, processing and collection methods which allow living tissue to provide better and more sustained results.

Another object of the present invention is to provide improved tissue sampling, processing and collection methods which help to "reboot" the face with non-apoptotic primitive precursor adipocytes and stem cells.

Another object of the present invention is to provide improved tissue sampling, processing and collection methods which can be used in mesotherapy volume restoration to lessen sagging and youthen skin tissue.

Another object of the present invention is to provide improved tissue sampling, processing and collection methods which may be used with power assisted injector guns.

Another object of the present invention is to provide improved tissue sampling, processing and collection methods which can be used in conjunction with multi-needle injectors and rollers.

Another object of the present invention is to provide a more efficient, versatile, cost-effective, sterile method and system for refining adipose tissue samples for immediate transplantation.

Another object of the present invention is to provide improved tissue sampling, processing and collection devices which are realized as disposable, single use small volume collection, processing and reinjection devices for manual subcutaneous tissue sampling and re-injection Another object of the present invention is to provide improved reusable small, medium and large volume collection, processing, and reinjection devices employing single use disposable components.

Another object of the present invention is to provide improved tissue sampling, processing and collection devices for use in bone marrow harvesting & processing operations carried out intra-operatively on live patient donors, or on deceased human donors on a post-mortem basis.

Another object of the present invention is to provide disposable, single use small volume manual collection, processing and reinjection devices.

Another object of the present invention is to provide reusable small, medium and large volume collection, processing, and reinjection devices that are used in conjunction with air or electrically powered hand-held tissue aspiration instruments, and also employing single use disposable components.

Another object of the present invention is to provide a disposable device for the refinement of adipose tissue.

Another object of the present invention is to provide a more efficient, cost-effective, sterile method and system that overcomes the deficiencies of prior devices and systems for the refinement of adipose tissue for autologous adipose transplantation.

Another object of the present invention is to provide surgeons with an improved method of and apparatus for harvesting tissue for autologous adipose transplantation.

Another object of the present invention is to provide an improved method and apparatus of harvesting, processing and collecting tissue for use in immediate clinical applications, as well as support of individuals engaged in cell-based science, developmental biology, tissue engineering research and genetic engineering.

These and other objects and advantages of the present invention will become apparent hereinafter and the claims to invention appended hereto.

BRIEF DESCRIPTION OF THE DRAWINGS

The above objects of the present invention will be more fully understood when taken in conjunction with the following figure Drawings, wherein like elements are indicated by like reference numbers, wherein:

FIG. 2A1 is a perspective view of a tissue collection tube employed in the tissue sampling, processing and collection devices of the present invention shown in FIGS. 9B and 13C, comprising a distal end opening for receipt of a distal tip capping element (i.e. cap), an proximal end opening for receiving a rubber plunger connected to a push shaft (or piston) shown in FIG. 2A2, and two sets of micro-pores formed along one side of the collection tube for allowing fluids to pass therethrough and concentrating cellular material, when un-occluded by the rotatable micro-pore occluder shown in FIG. 2C;

FIG. 2A2 is a perspective view of a rubber plunger connected to a push shaft (i.e. piston), which is adapted to slide into the interior volume of the tissue collection tube shown in FIG. 2A1; FIG. 2A3 is a perspective view of the micro-pore occluder that slides on and fits about the tissue collection tube shown in FIG. 2A1, and which can be rotatably configured to occlude the micro-pores in its occluded state, or allow the micro-pores to remain exposed and open to the ambient environment;

FIG. 2A4 is a perspective view of the cap adapted to fit over and close off (i.e. create fluid seal over) the distal end opening or tip of the tissue collection tube shown in FIG. 2A1;

FIG. 3 is a perspective view showing the assembly of the components of the tissue sampling, processing and injection syringe device of the present invention, depicted in FIGS. 2, 7A, 11A, and 15A;

FIG. 5 is a flow chart describing the primary steps carried out when practicing the method of harvesting a tissue sample from a patient or donor using the tissue sampling, processing and injection syringe device of the present invention, shown in FIGS. 2 through 4B;

FIG. 5D1 is a perspective view of the tissue sampling, processing and injection syringe device of FIG. 2, showing its plunger being drawn back from the tissue sampling, processing and injection syringe device (from state 1 to state 2) to create vacuum pressure within the tissue collection tube and aspirate a sample of fat tissue therein;

FIG. 5D2 is a perspective view of the tissue sampling, processing and injection syringe device of FIG. 2, being used to aspirate fat tissue sample, by surgeon inserting the syringe device, with micro-pores occluded, and cannula mounted, into desired donor or treatment site, and maintaining backward pressure on plunger/piston to create vacuum, and aspirate a sample of fat tissue from a patient or donor;

FIG. 6 is a flow chart describing the primary steps carried out when practicing the method of processing aspirated tissue sample using the tissue sampling, processing and injection syringe device of the present invention shown in FIG. 2;

FIGS. 6B1 through 6B6 set forth a series of illustrations showing the tissue sampling, processing and injection syringe device of FIG. 2 being manually reconfigured from (i) its occluded state shown in FIG. 6B1, during which a sample of tissue can be aspirated/sampled into the collection tube when the plunger is manually withdrawn from its collection barrel while its micro-pores are occluded (i.e. blocked) and ejected from the collection tube when the plunger is pushed into the collection tube while the micro-pores are occluded, into (ii) its non-occluded state shown in FIG. 6B6, during which fluid in a collected tissue sample can be filtered/expressed through the micro-pores of the collection tube when the plunger is manually pushed into the collection tube while the micro-pores are non-occluded to concentrate the collected tissue sample for re-injection into a patient or subsequent processing at a tissue bank;

FIG. 7 is a flow chart describing the primary steps carried out when practicing the method of injecting processed tissue into a patient using the tissue sampling, processing and injection syringe device of FIG. 2;

FIG. 8 is a flow chart describing the primary steps carried out when practicing the method of harvesting, processing and injecting a tissue sample into a patient using the tissue sampling, processing and injection syringe device of the present invention, depicted in FIGS. 1 through 7D;

FIG. 9 is a flow chart describing the primary steps involved when practicing the method of harvesting tissue samples from a patient using the 3-pack tissue sampling, processing and collection device of the present invention shown in FIGS. 9A and 9B, being connected in-line with hand-held tissue aspiration instrument;

FIG. 9A is a perspective view of the 3-pack tissue sampling, processing and collection device of the present invention being prepared for connection in-line with a hand-held power-assisted tissue aspiration instrument, by removing its barbed connector for connection of the 3-pack tissue sampling, processing and collection device;

FIG. 9E is a cross-sectional diagram of the 3-pack tissue sampling, processing and collection device shown in FIG. 9D, illustrating how aspirated tissue flows from the input side, through the micro-pores formed in the walls of the tissue collection tubes mounted within the device, and out through the vacuum source side of the system, to leave concentrated tissue samples in the collection tubes, prepared for immediate reinjection into the body of the donor patient, or other patient requiring tissue injection;

FIG. 10 is a flow chart describing the steps carried out when practicing the method of processing aspirated tissue during harvesting using the 3-pack tissue sampling, processing and collection device of the present invention, coupled in-line to a hand-held powered tissue aspiration instrument;

FIG. 11 is a flow chart describing the primary steps carried out when practicing the method of injecting processed tissue samples into a patient using a fat-filled tissue injection syringe device of present invention assembled using a fat-filled tissue collection tube from the device of FIG. 10A, to be converted into the tissue injection syringe device shown in FIG. 2;

FIG. 11C is a perspective view of the fat-filled tissue injection syringe device of present invention being used to inject processed tissue back into the patient to achieve a desired achieve correction;

FIG. 12 is a flow chart describing the primary steps carried out when practicing the method of harvesting, processing and injecting a tissue sample into a patient using the tissue sampling, processing, collection and injection device, depicted in FIGS. 9 through 11D;

FIG. 13 is a flow chart describing the primary steps carried out when practicing the method of sampling aspirated tissue samples using 6-pack tissue sampling, processing and collection device of the present invention, shown in FIGS. 13A and 13B, allowing the surgeon to select which collection tubes to fill at any given moment, while coupled in-line with a hand-held tissue aspiration instrument;

FIG. 13F is a perspective view of the six-pack tissue sampling, processing and collection device connected to a hand-held power-assisted tissue aspiration instrument of the present invention by way of a second of flexible tubing;

FIG. 14 is a flow chart describing the primary steps carried out when practicing the method of processing aspirated tissue during harvesting using the six-pack tissue sampling, processing and collection device of the present invention, shown in FIGS. 13A and 13B;

FIG. 15 is a flow chart describing the primary steps carried out when practicing the method of injecting processed tissue into a patient using a fat-filled tissue injection syringe device of the present invention which is constructed by attaching a flanged occluder to the tissue collection tube and inserting a plunger and piston into the proximal end opening of the tissue collection tube, shown in FIGS. 3, 5C, and 15A;

FIG. 15B is a perspective view of the fat-filled tissue injection syringe device of present invention constructed in FIG. 15A, shown being used by a surgeon to inject tissue into a patient by depressing the piston into the collection tube while its micro-pores are in their occluded state;

FIG. 16 is a flow chart describing the primary steps carried out when practicing the method of harvesting, processing and injecting a tissue sample into a patient using the tissue sampling, processing, collection and injection devices of the present invention, depicted in FIGS. 13 through 15D.

DETAILED DESCRIPTION OF THE ILLUSTRATIVE EMBODIMENTS OF THE PRESENT INVENTION

Figure 1:
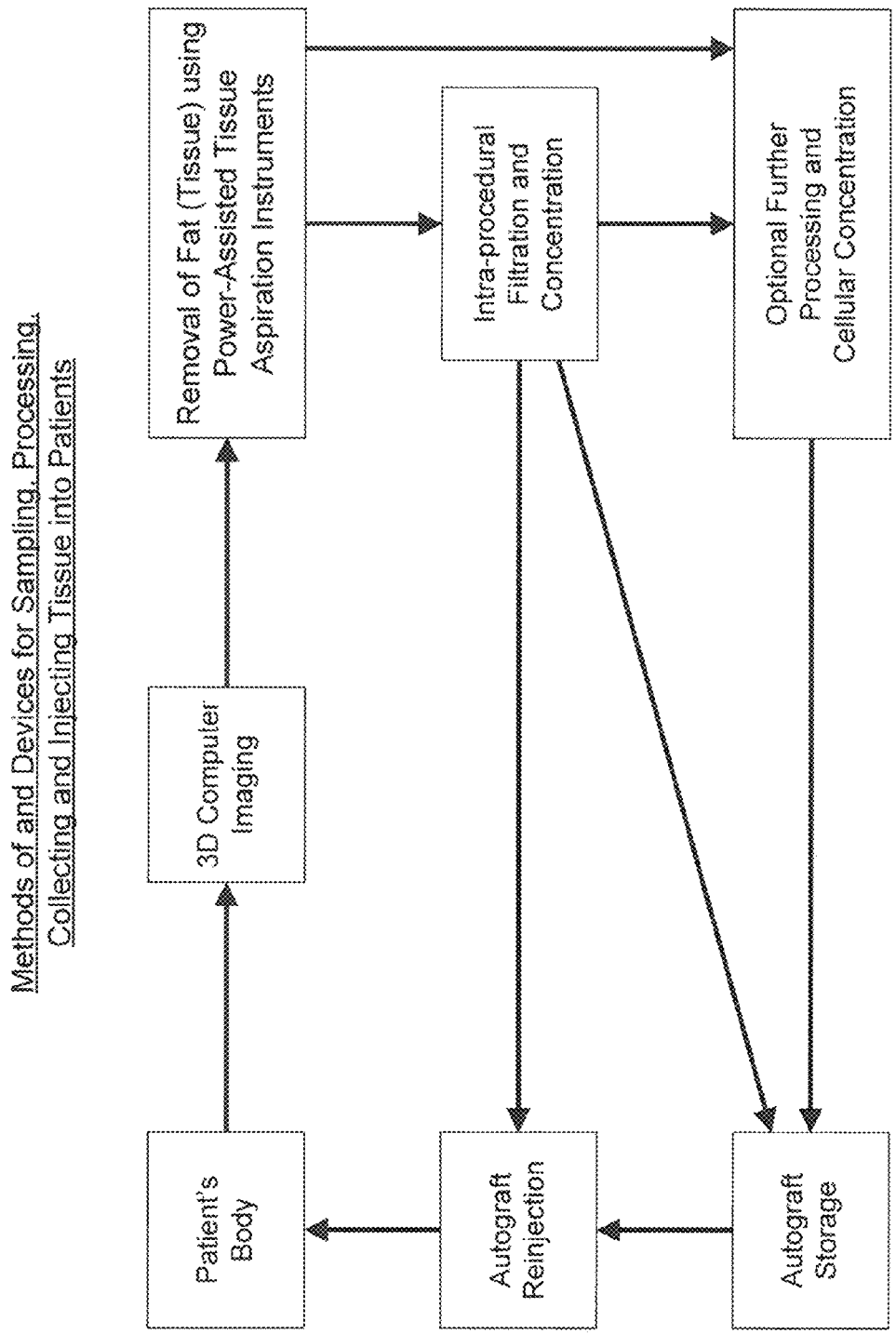
FIG. 1 is a graphical illustration showing the various phases of tissue sampling, collection, processing and re-injection using the devices and methods of the present invention.

Referring to the figures in the accompanying Drawings, the various illustrative embodiments of the present invention will be described in great technical detail, wherein like elements will be indicated using like reference numerals.

Overview of the Methods and Apparatus of the Present Invention

The illustration in FIG. 1 shows the various phases of tissue sampling, collection, processing and re-injection using the modular devices and methods of the present invention disclosed herein, wherein modular, disposable tissue aspiration, processing, collection and/or re-injection components can be used in different tissue sampling, processing and collection system designs, providing significant improvements in flexibility, convenience, and economy.

In the case of cosmetic surgical planning, in particular, 3D computer imaging techniques are typically used to survey a patient's body contour and plan out fat tissue transplantation for corrective purposes.

As shown, tissue is harvested in small volumes from the patient/donor using the tissue sampling, processing and injection syringe device 2 with cannula 3, forming device 1, shown and described FIGS. 2 through 5E.

Alternatively, tissue is harvested in medium or large volumes using either 3-pack tissue sampling, processing and collecting device of the present invention shown in FIGS. 9A through 9E, or the 6-pack tissue sampling, processing and collecting device of the present invention shown in FIGS. 13A through 13F, each being connected in-line to outlet port of a hand-supportable power-assisted tissue aspiration instrument 10 as disclosed in Applicant's copending U.S. application Ser. Nos. 12/850,786, 12/462,596 and 12/813,067, incorporated herein by reference.

Figure 3:
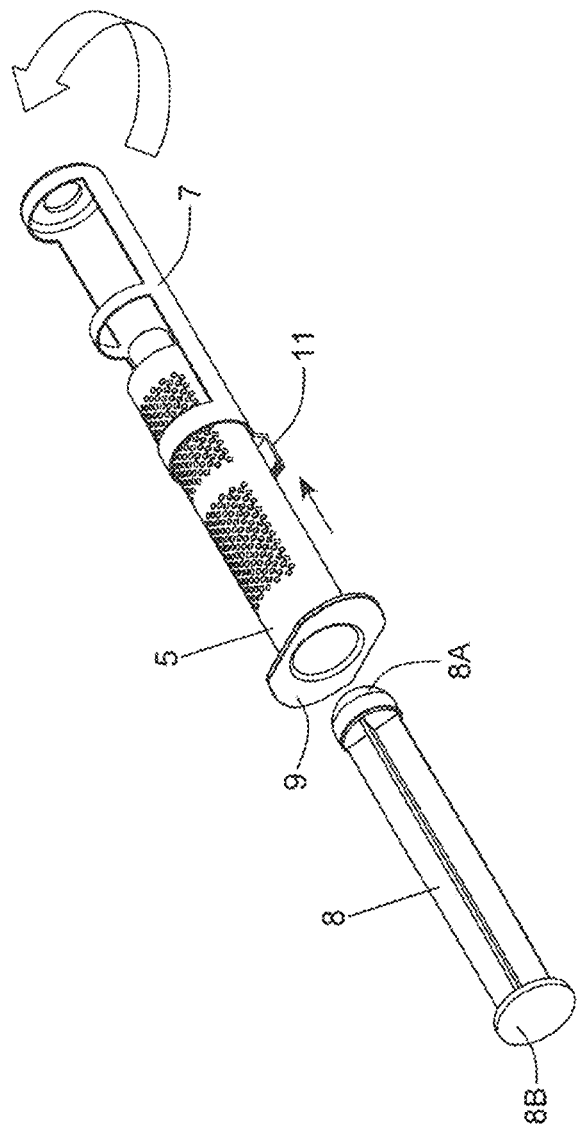
Figure 5A:
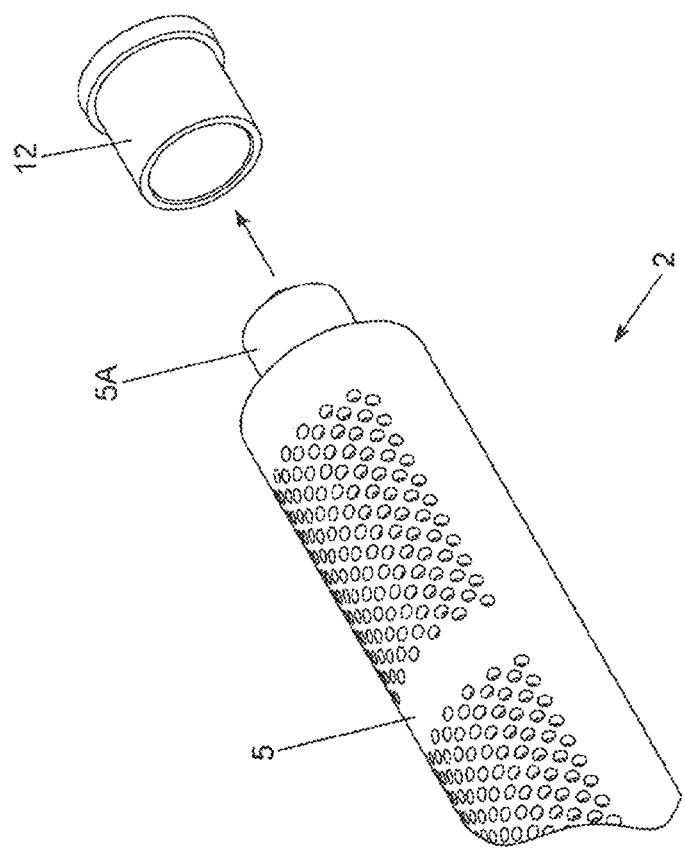
FIG. 5A is a partially cut-away perspective view of the tissue sampling, processing and injection syringe device of FIG. 2, showing its cap being removed from its distal end opening.
Figure 5B:
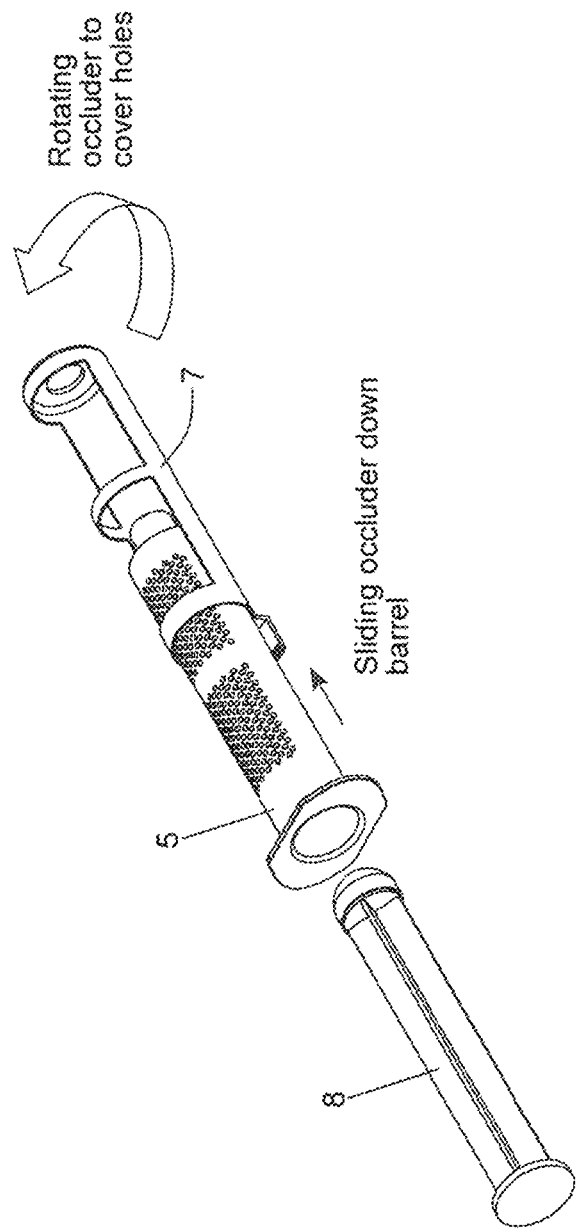
FIG. 5B is a perspective view of the tissue sampling, processing and injection syringe device of FIG. 2, showing its occluder being slid down its collection barrel and rotating same to cover the micro-pores of the tissue sampling, processing and injection syringe device of the present invention.

In either case, fat tissue is collected in individual tissue collection tubes 5 having micro-pores 6 which are selectively occluded or non-occluded simply by rotation of a micro-pore occluder 7 that snap fits about the tissue collection tube, as shown in FIGS. 3 and 5B.

In the case of the tissue sampling, processing and injection syringe device 2 shown and described FIGS. 2 through 5E, a single tissue collection tube 5 is filled with fat tissue during manually powered aspiration operations, illustrated in FIGS. 5D1, 5D2, and 5E.

Figure 9B:
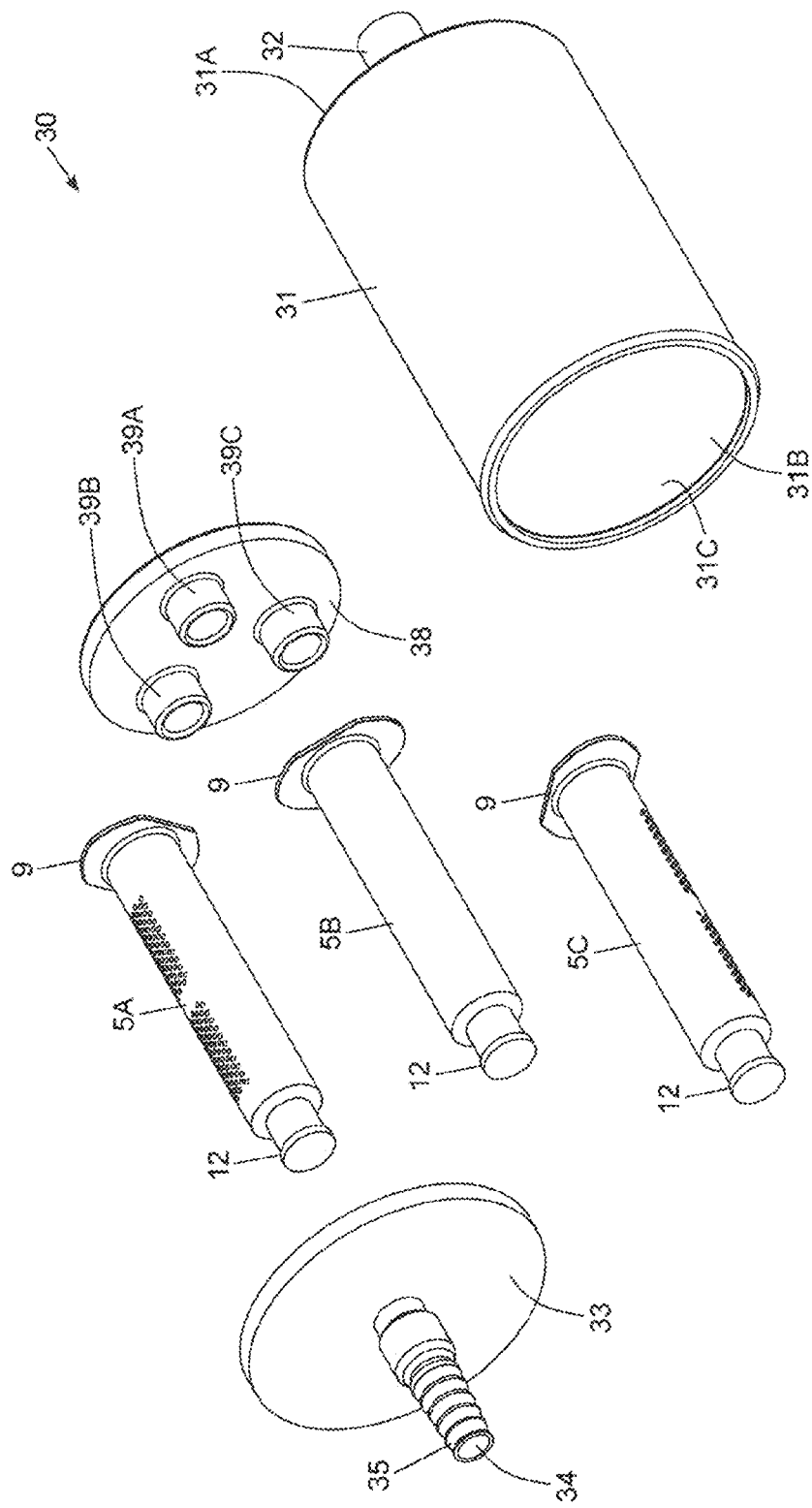
FIG. 9B is a perspective exploded view of the 3-pack tissue sampling, processing and collection device of FIG. 9A, shown comprising a lid with a barbed connector (provided on the vacuum side), a 3-syringe base plate suction mount for mounting three syringe collection tubes, and a chamber with a screw-on connector to mount directly on rear of hand-held tissue aspiration instrument.
Figure 9C:
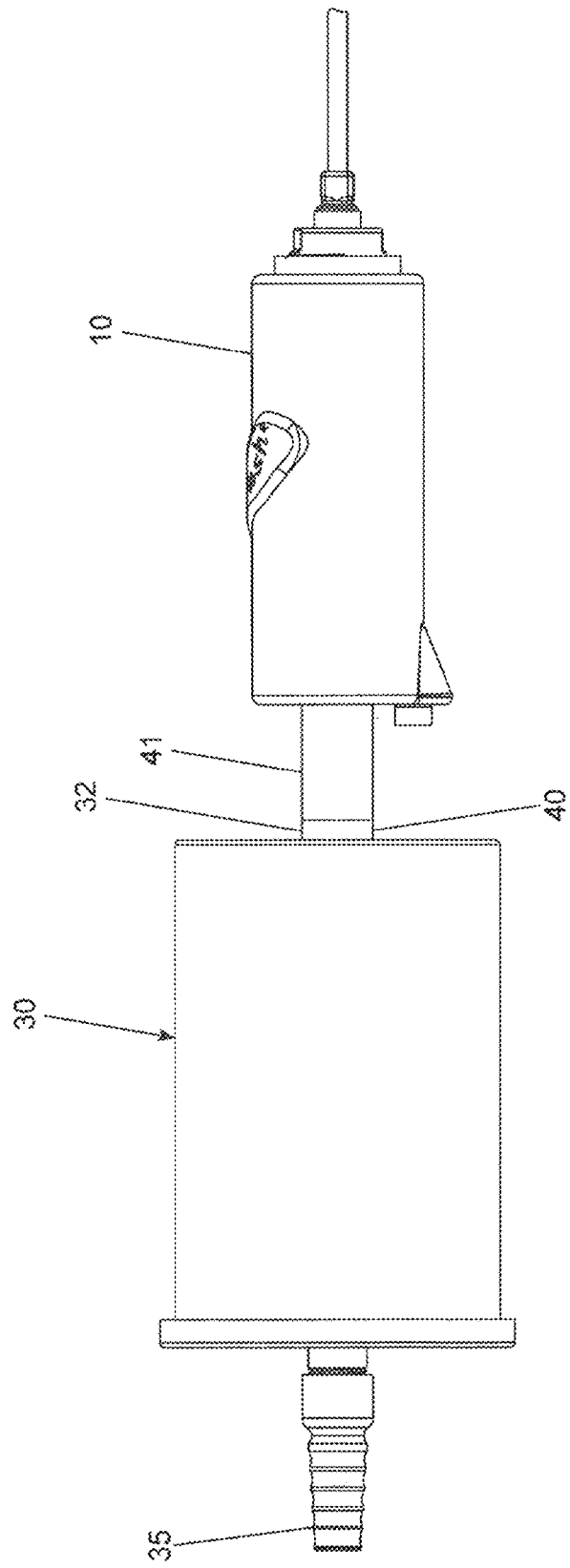
FIG. 9C is a perspective view of the 3-pack tissue sampling, processing and collection device of the present invention shown completely assembled, and connected to a hand-supportable power-assisted tissue aspiration instrument.
Figure 9D:
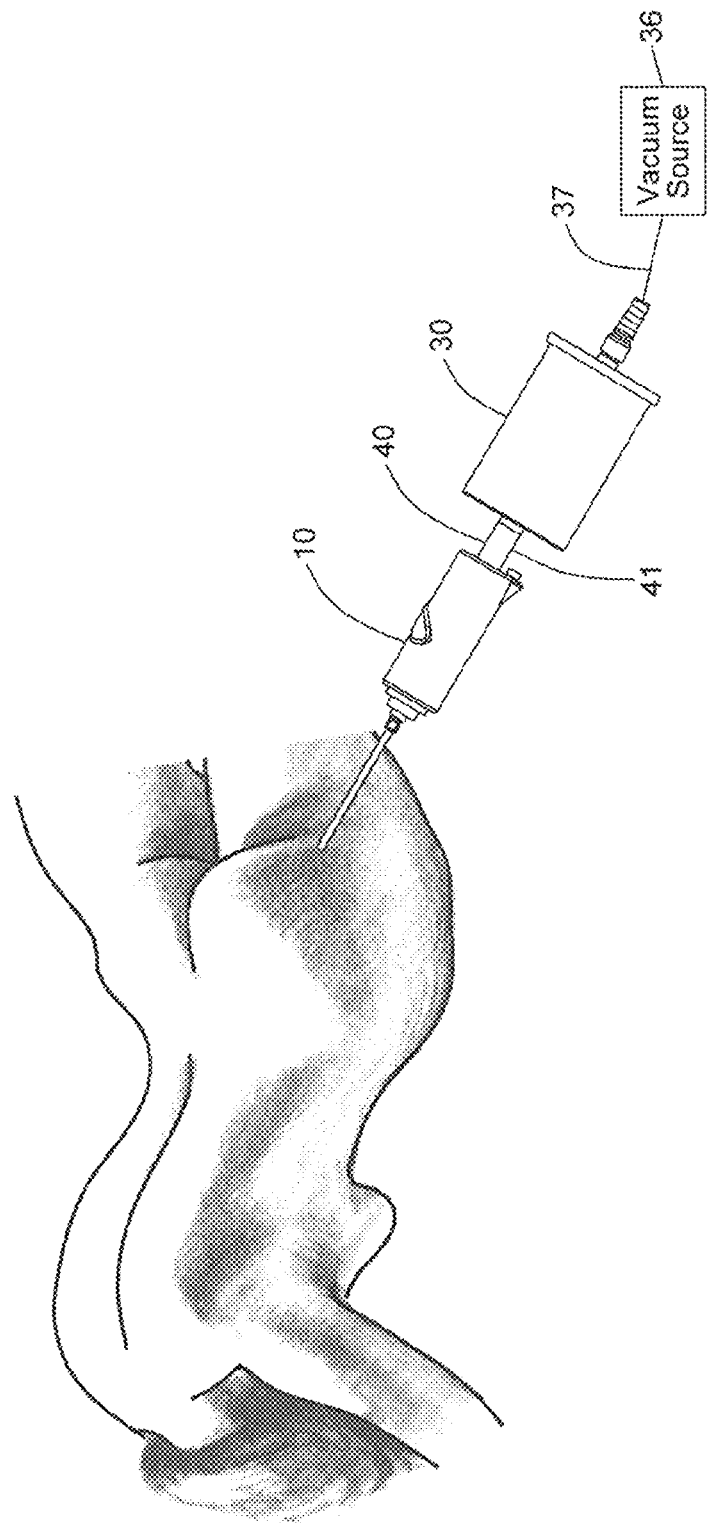
FIG. 9D is a perspective exploded view of the 3-pack tissue sampling, processing and collection device of the present invention, connected to a vacuum source by way of the hand-supportable power-assisted tissue aspiration instrument, while aspirating tissue samples from a patient, and filtering the same during aspiration to produce concentrated tissue prepared for immediate re-injection into the patient, or subsequent processing at a tissue bank.
Figure 10A:
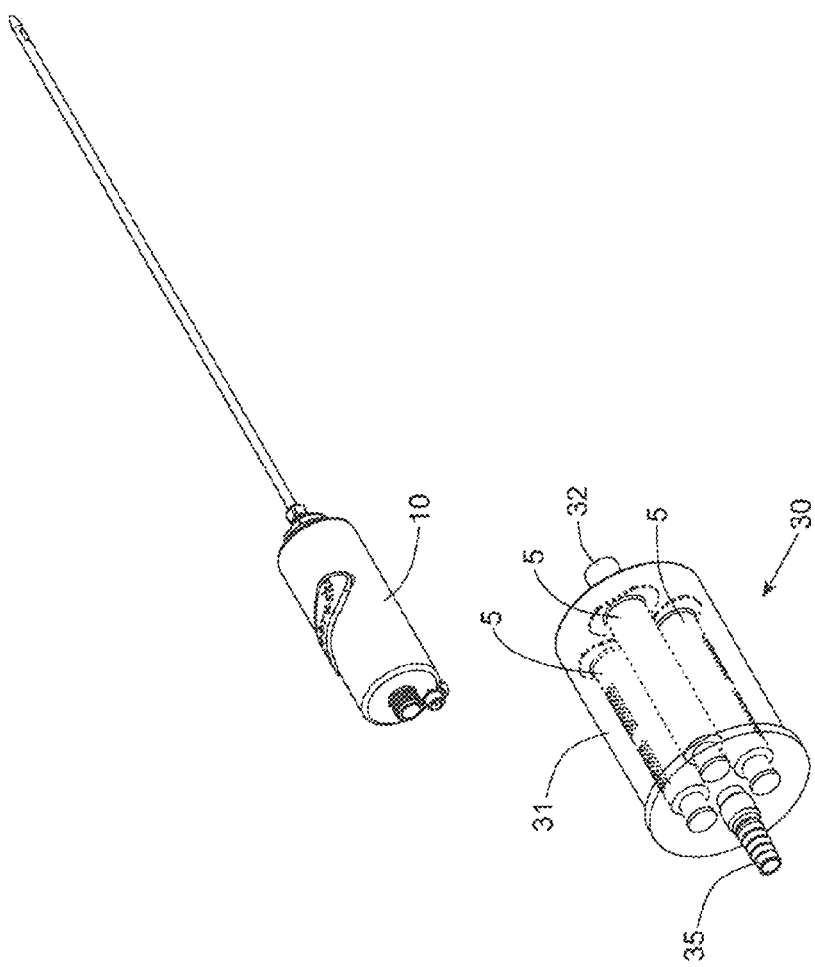
FIG. 10A is a perspective view of the 3-pack tissue sampling, processing and collection device shown in FIG. 9D, being detached from the hand-supportable powered tissue aspiration instrument.
Figure 10B:
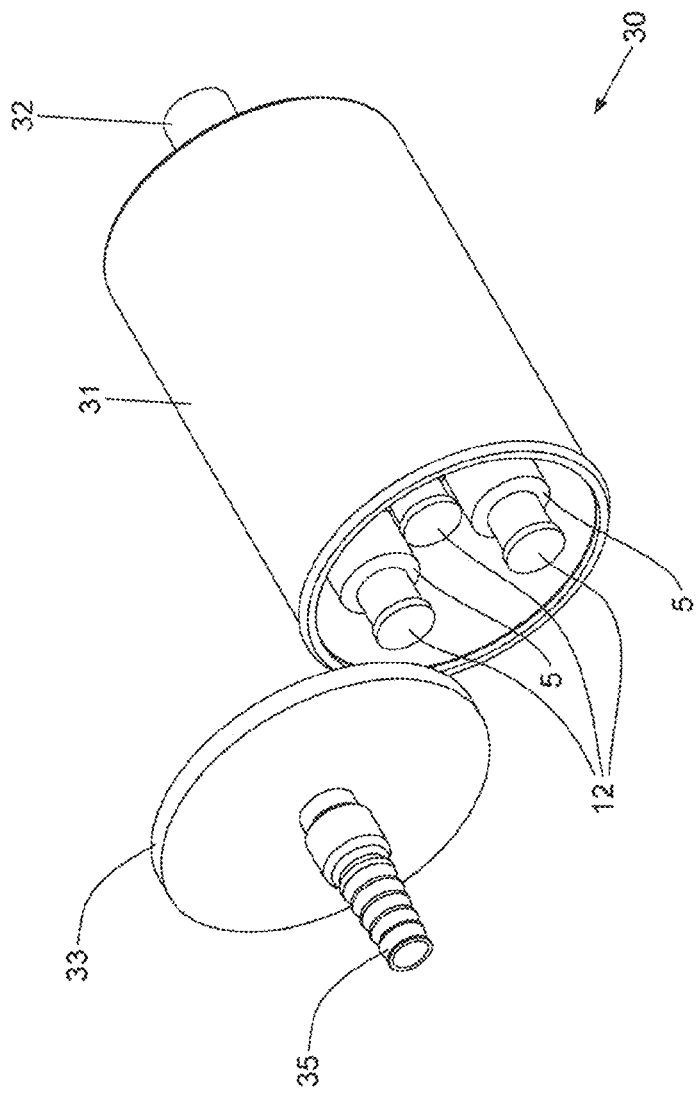
FIG. 10B is a perspective view of the 3-pack tissue sampling, processing and collection device shown in FIG. 9D, shown with its lip being removed to provided access to the tissue-filled collection tubes contained within the container housing.
Figure 10C:
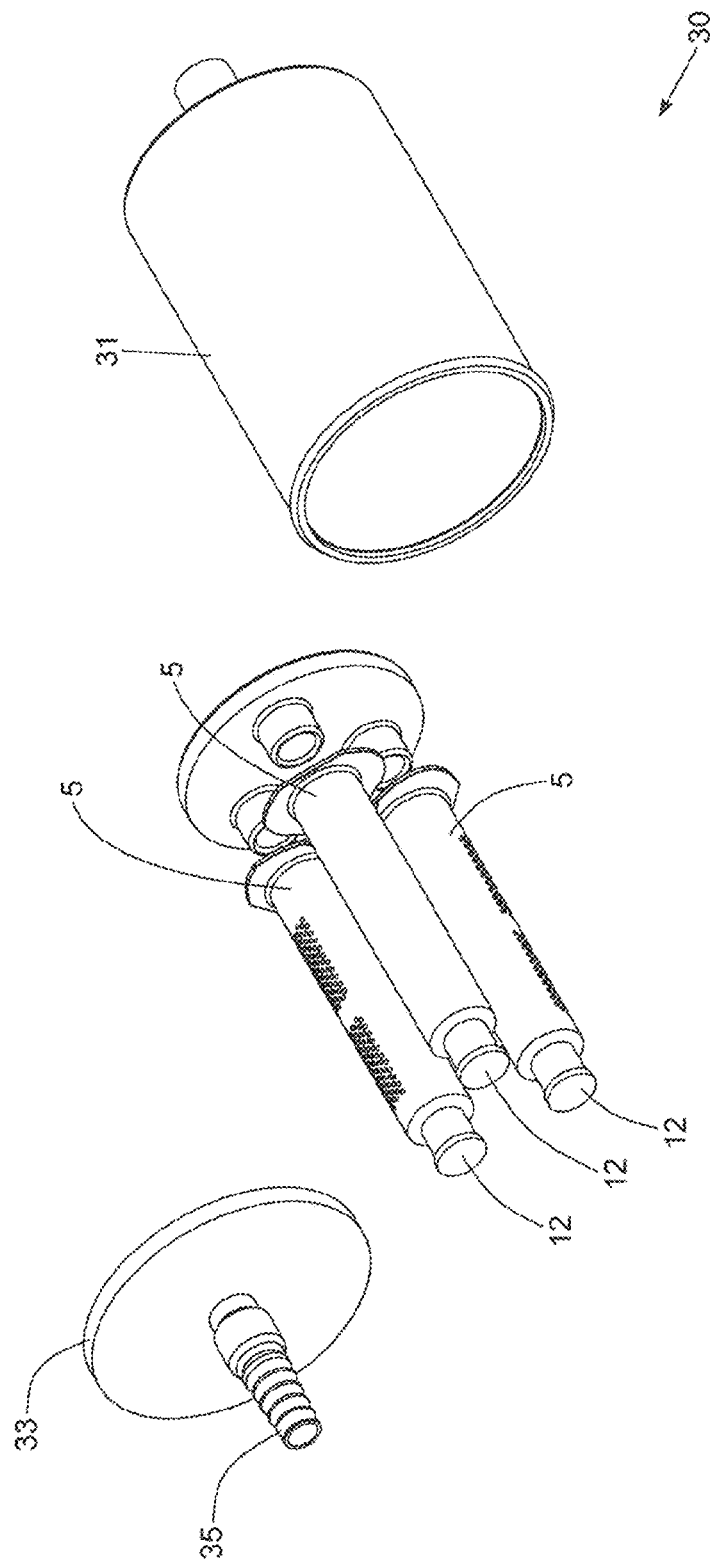
FIG. 10C is a perspective view showing the removal of the tissue collection tubes from the 3-pack tissue sampling, processing and collection device of the present invention.
Figures 13A, 13B:
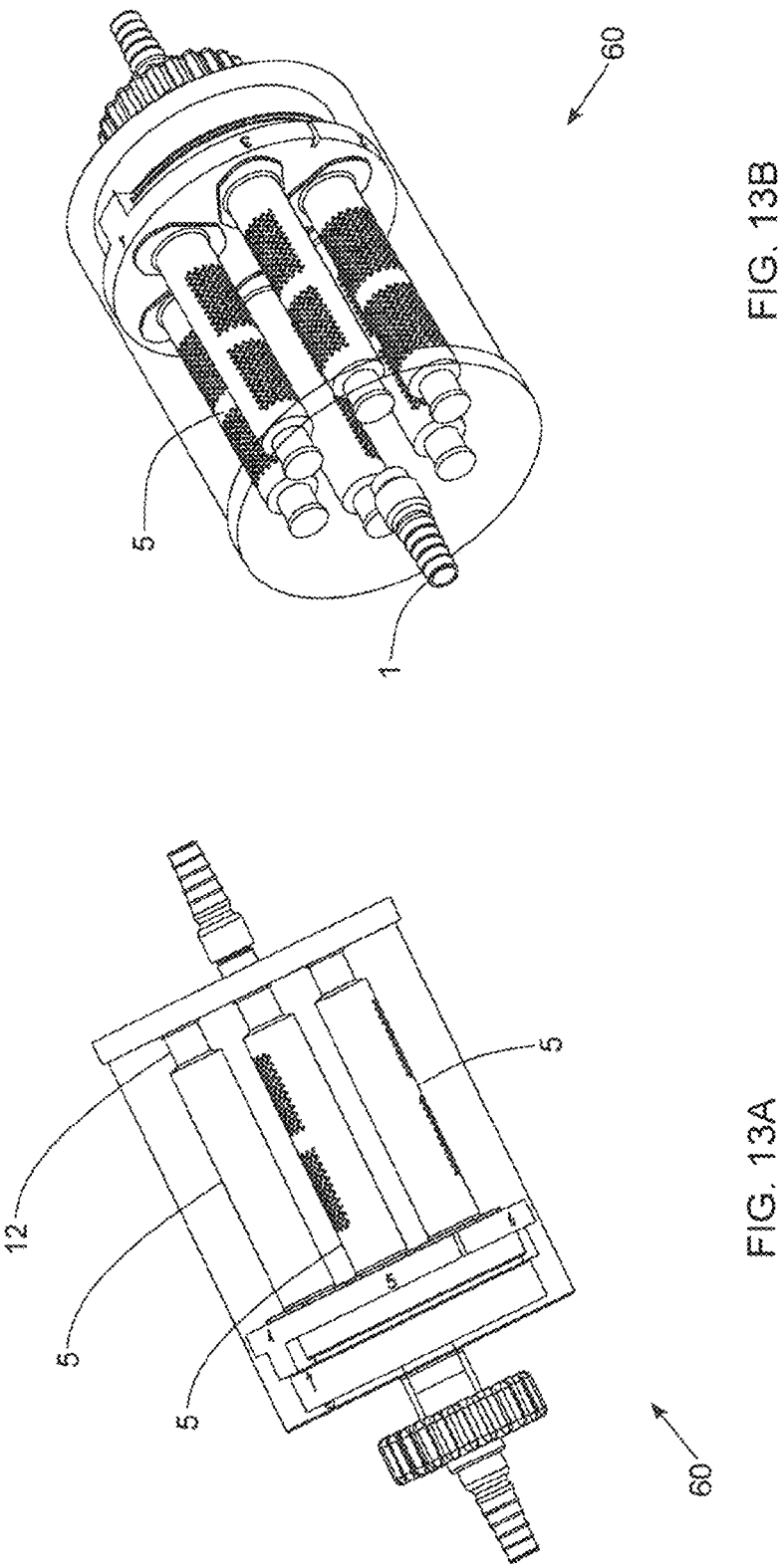
FIG. 13A is a first perspective view of the 6-pack tissue sampling, processing and collection device of the present invention shown completely assembled, adapted for in-line connection with a hand-held power-assisted tissue aspiration instrument, and having six separate tissue collection tubes (i.e. chambers) which may be independently selected by the surgeon, by the manual rotation of the selector knob, and then filled with tissue biopsy or aspirate from different areas within a patient during surgical operations.
FIG. 13B is a second perspective view of the 6-pack tissue sampling, processing and collection device shown in FIG. 13A.
Figure 13C:
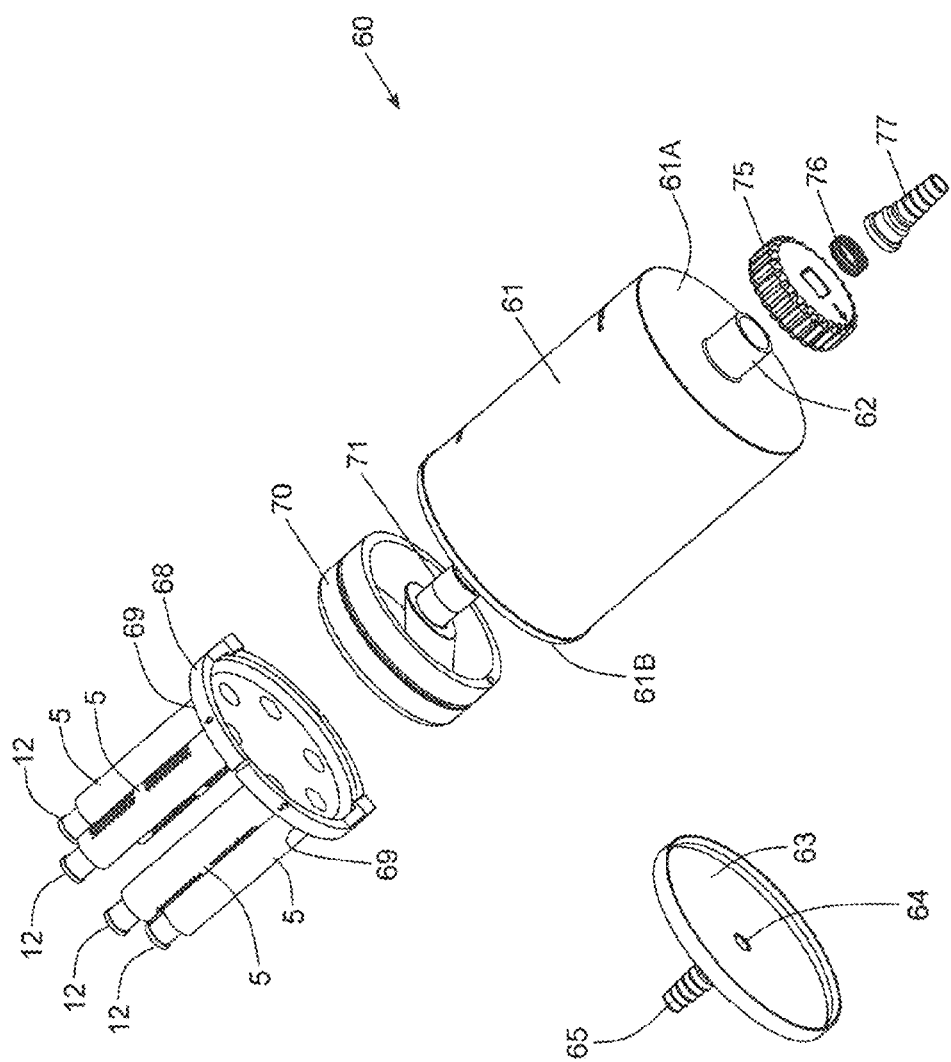
FIG. 13C is a first exploded perspective view of the 6-pack tissue sampling, processing and collection device shown in FIGS. 13A and 13B, shown comprising a collection chamber, a lid with barbed connector for connection to the suction tubing, a suction plate having six projections for supporting six tissue collection tubes (i.e. within the collection chamber), a selector with a passageway/flowpath extending from the center of the chamber to periphery thereof to control the flow of aspirated fat sample into the selected tissue collection tube, and a barbed connector for connecting to tubing extending to the hand-supportable tissue aspiration instrument, and a spring pushing up the turning knob and keeping the selector at the bottom of the collection chamber.
Figure 13D:
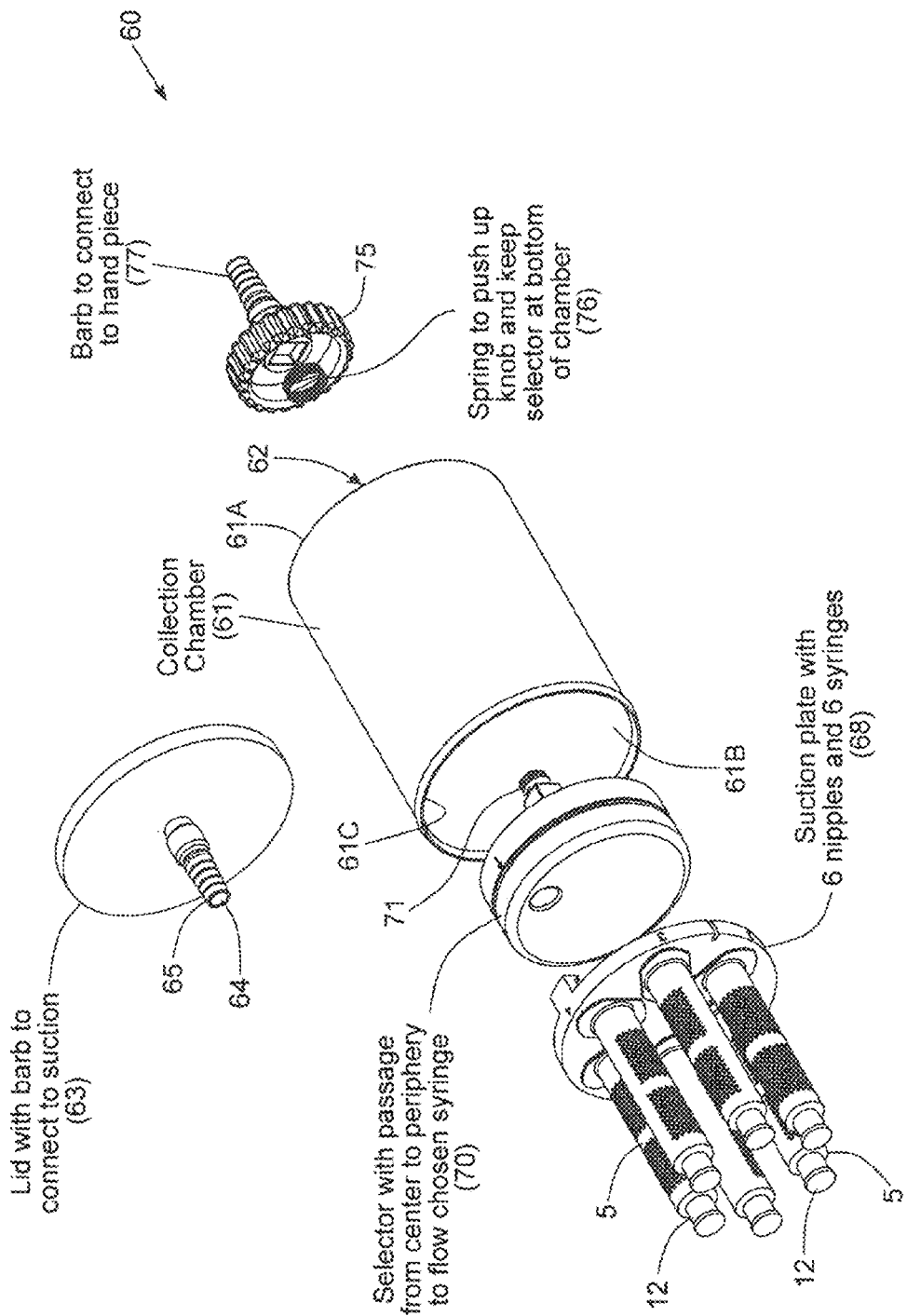
FIG. 13D is a second exploded perspective view of the 6-pack tissue sampling, processing and collection device shown in FIGS. 13A, 13B and 13C.
Figure 13E:
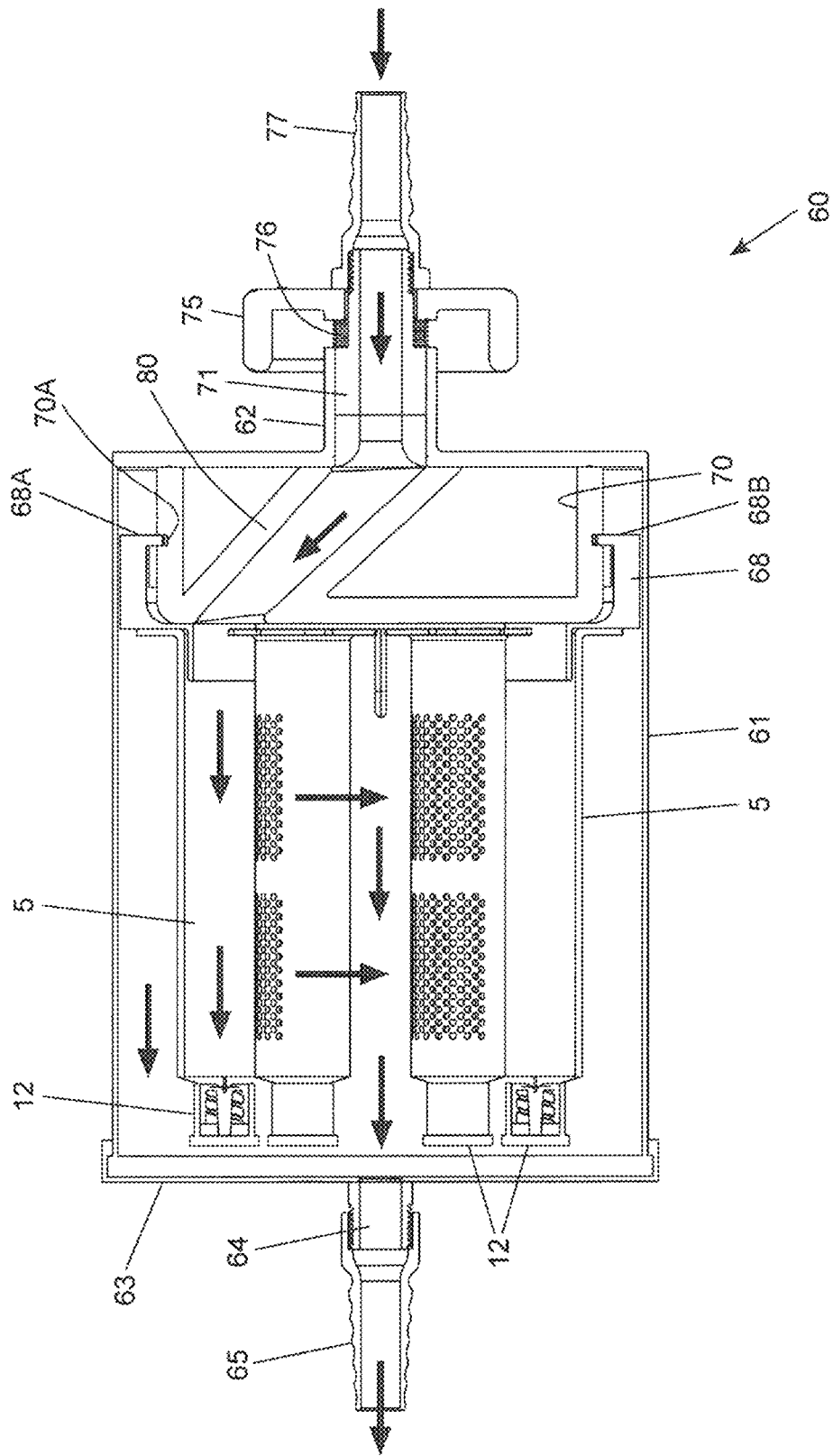
FIG. 13E is a cross-sectional view of the in-line tissue sampling, processing and collection device shown in FIGS. 13A through 13D, illustrating the passage of aspirated tissue within the selector component, extending from the center of the device to the periphery thereof to control the flow of aspirated fat samples into the selected syringe.
Figure 14A:
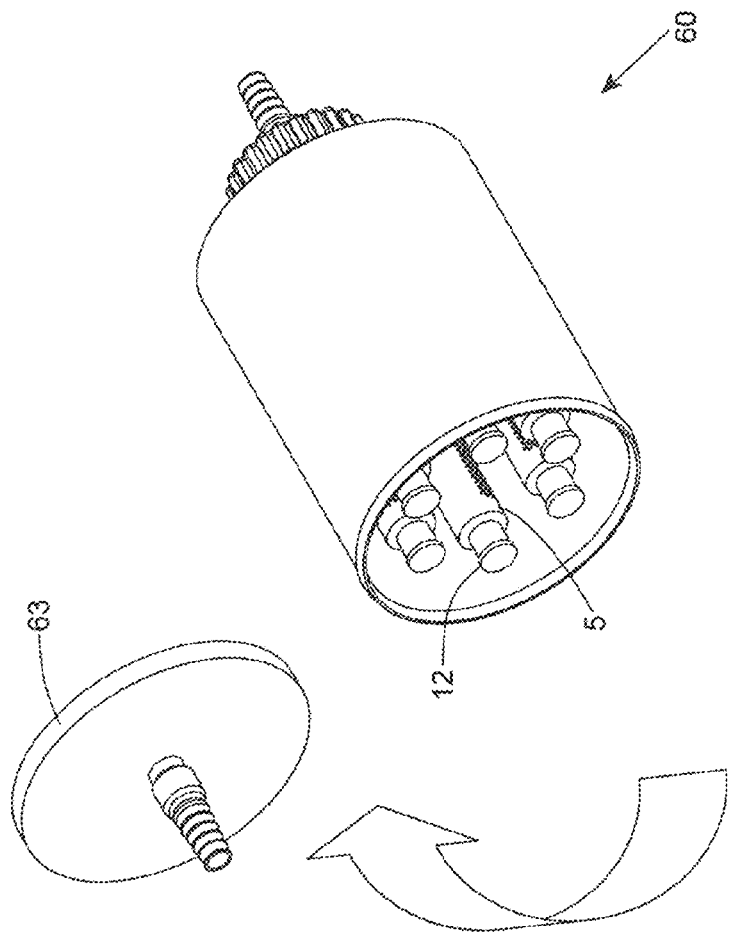
FIG. 14A is a perspective view of the six-pack tissue sampling, processing and collection device of the present invention, showing its collection lid being removed after the device has been disconnected from the hand-hand power-assisted tissue aspiration instrument shown in FIG. 13F.
Figure 14B:
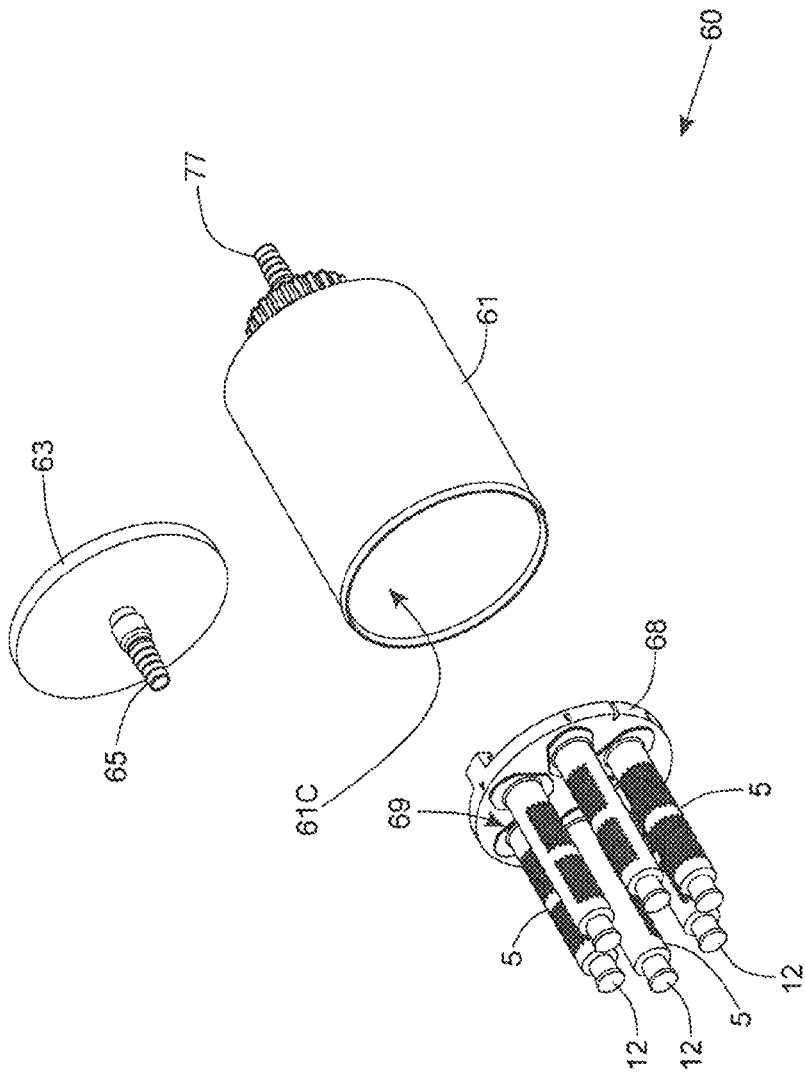
FIG. 14B is a perspective view of the six-pack tissue sampling, processing and collection device of the present invention, showing the removal of the tissue collection tube suction plate from the collection chamber of the six-pack tissue sampling, processing and collection device.
Figure 14C:
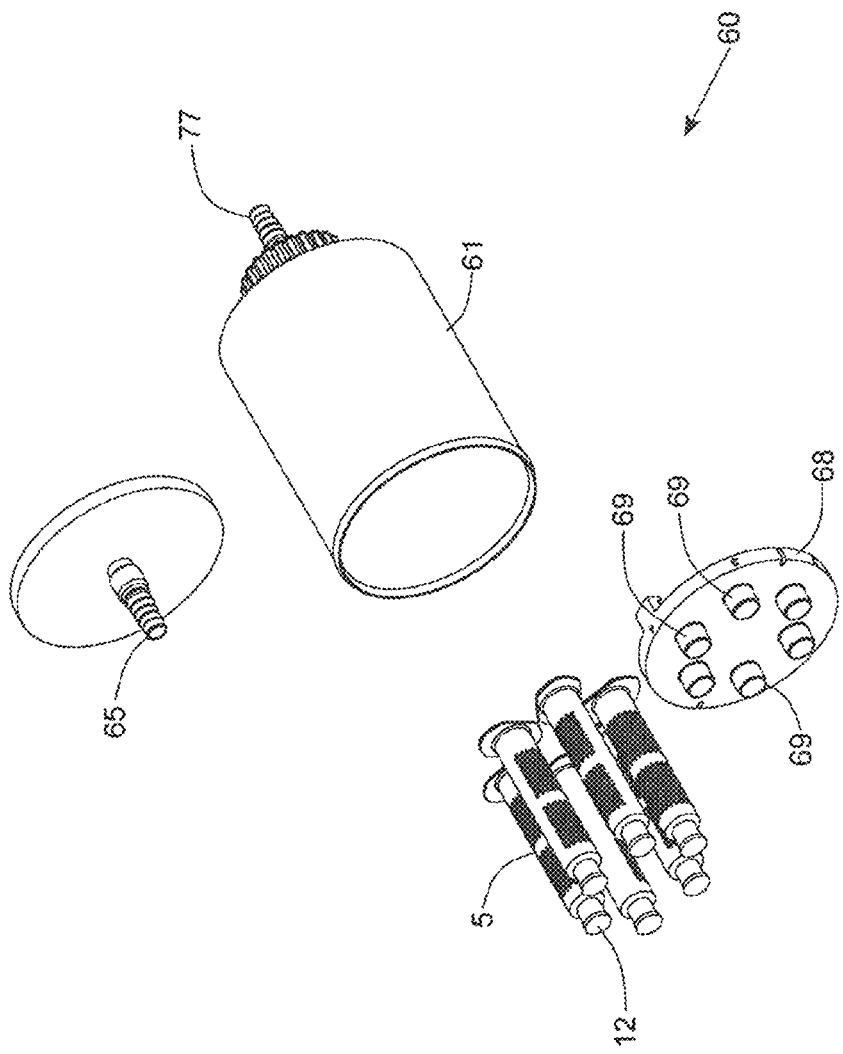
FIG. 14C is a perspective view of the six-pack tissue sampling, processing and collection device of the present invention, showing the detachment of the tissue collection tubes (i.e. syringe barrels) from the tissue collection tube suction plate.

In the case of the 3-pack tissue sampling, processing and collecting device of the present invention shown in FIGS. 9A through 9E, or the 6-pack tissue sampling, processing and collecting device of the present invention shown in FIGS. 13A through 13F, the multiple tissue collection tubes 5, shown in FIG. 2A1, without a micro-occluder 7 installed, are supported on the mounting posts of (i) suction mounting plate 38 within the collection chamber of the 3-pack device 30 shown in FIGS. 9B and 10C, and (ii) suction plate 68 within the collection chamber of the 6-pack device shown in FIGS. 13C and 14C.

Figure 2:
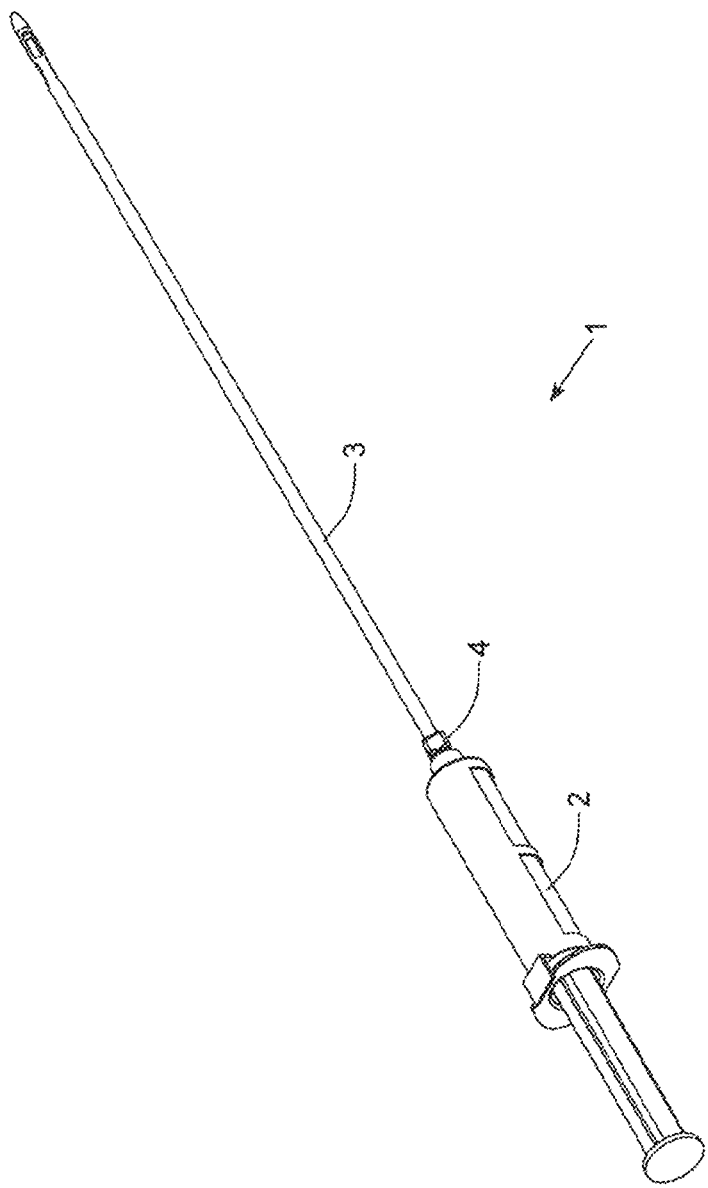
FIG. 2 is a perspective view of an illustrative embodiment of the tissue sampling, processing and injection syringe device of the present invention, to which a cannula is connected via a Leur locking connector.

As will be described in greater detail hereinafter, each tissue collection tube 5 used to construct the tissue sampling, processing and injection syringe device of FIG. 2, is also used in multiples within the 3-pack and 6-pack tissue sampling, processing and collection devices of FIGS. 9A and 13A.

As shown in FIG. 2A1, the tissue collection tube 5 has the appearance of a syringe barrel, with micro-pores 6 formed in the tube walls normally open for fluid filtration therethrough during tissue collection operations. Each tissue collection tube 5 has a distal end opening 5A adapted to receive a cannula 3 via a Leur lock connector fitting 4, and a proximal end opening 5B adapted to receive a plunger 8A and piston 8B subassembly 8. Each tissue collection tube 5 is also adapted with a flange 9 having opposite flat side edge surfaces 9A and 9B, for engagement with a flat rectangular flange 11 extending from the micro-pore occluder 7, as shown in FIGS. 2A2 and 3.

As shown in FIG. 3B, the micro-pore occluder 7 is slid around and rotatable about the tissue collection tube, in either one of two possible configurations. When the micro-occluder 7 is arranged in its micro-pore occlusion state shown in FIG. 4A, and a vacuum is applied at the proximal end opening, tissue can be aspirated into the tissue collection tube. When the micro-occluder 7 is arranged in its micro-pore non-occlusion state shown in FIG. 4B, a cap 12 is applied to the distal tip of the tissue collection tube 5 and pressure is applied against a collected tissue sample in the tissue collection tube (i.e. by pushing its plunger and piston into the tissue collection tube), fluid is expressed out of the micro-pores 6 formed in the side walls of the tissue collection tube, filtering and concentrating the cellular in situ within the collection tube.

Several options are available after tissue samples have been collected and processed within individual tissue collection tubes within the collection chamber of multi-pack tissue sampling, processing and collection device 30 or 60.

A first option is to readily adapt each tissue-filled collection tube into a tissue injection syringe device by capping their distal end openings with cap 12, and inserting a plunger piston 8 partially into the proximal end openings thereof. Then these tissue-filled injection syringe devices 2 can be placed in autograft storage, or used immediately in autograft tissue re-injection procedures by simply removing the cap from the distal end opening of the syringe device and connecting a cannula thereto via Leur locking mechanism. Alternatively, the tissue collection tubes, filled with filtered and concentrated cellular material, can be subjected to further processing and cellular concentration, prior to being place in autograft storage. Thereafter, the tissue collection tubes can be removed from autograft storage and used in autograft tissue re-injection procedures.

Once the surgeon makes use of autograft injections to achieve corrections in the patient, 3D computer imaging is used again to see how closely the surgeon was able to achieve planned body sculpting during a first round of surgery. If necessary, the surgeon can repeat the phases indicated in FIG. 1 to achieve desired results.

Having provided an overview of the apparatus and methods of the present invention, it is appropriate at this juncture to describe the same in greater technical detail below.

Specification of the Tissue Sampling, Processing and Injection Syringe Device of the Present Invention FIG. 2 shows an illustrative embodiment of the tissue sampling, processing and injection syringe device of the present invention 2, to which a cannula 3 is connected via a Leur locking connector 4. The components of this syringe device 2 are shown in FIGS. 2A through 2D, as comprising: tissue collection tube 5 having (i) distal end opening 5A for receipt of distal tip capping element (i.e. cap) 12, (ii) proximal end opening 5B and (iii) interior volume 5C; a rubber plunger 8A connected to a push shaft (or piston) 8B shown in FIG. 2B, for insertion into the interior volume 5C; two sets of micro-pores 6A and 6B formed along one side of the collection tube for allowing fluids to pass therethrough and concentrating cellular material, when un-occluded by the rotatable micro-pore occluder shown in FIG. 2C; and micro-pore occluder 7 sliding on and fitting about the tissue collection tube 5, and being rotatably configured to occlude its micro-pores 6 in its occluded state, or allow its micro-pores 6 to remain exposed and open to the ambient environment; and cap 12 adapted to fit over and close off (i.e. create fluid seal over) the distal end opening 5A, or tip portion of the tissue collection tube shown in FIG. 2A.

FIG. 3 shows the components of the tissue sampling, processing and injection syringe device 2, depicted in FIGS. 2, 7A, 11A, and 15A, being assembled in accordance with the principles of the present invention.

Figures 4A, 4B:
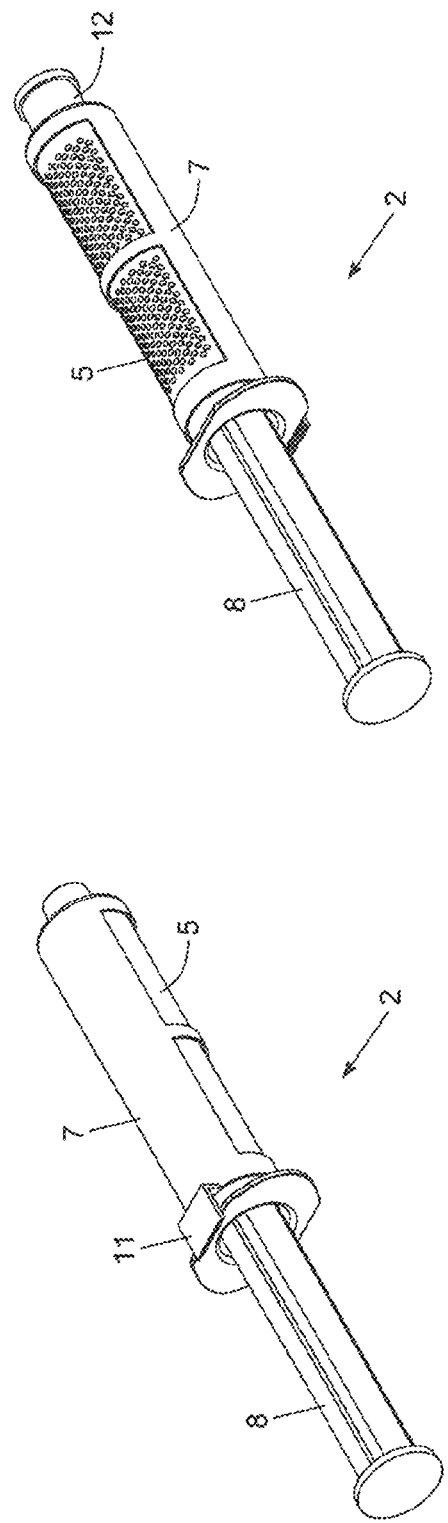
FIG. 4A is a perspective view of the tissue sampling, processing and injection syringe device of the present invention, shown configured with its micro-pores arranged in its occluded state.
FIG. 4B is a perspective view of the tissue sampling, processing and injection syringe device of the present invention, shown configured with its micro-pores arranged in its non-occluded state.

FIG. 4A shows the tissue sampling, processing and injection syringe device 2 of FIG. 2, arranged with its micro-pores in its occluded state, whereas FIG. 4B shows the tissue sampling, processing and injection syringe device of FIG. 2 arranged with its micro-pores in its non-occluded state.

Method of Harvesting a Tissue Sample from a Patient or Donor Using the Tissue Sampling, Processing and Injection Syringe Device of the Present Invention The flow chart of FIG. 5 describes the primary steps carried out when practicing the method of harvesting a tissue sample from a patient or donor using the tissue sampling, processing and injection syringe device of FIGS. 2 through 4B.

As indicated in Step 1 of FIG. 5, the tip cap 12 is removed from the syringe device 2 as shown in FIG. 5A.

As indicated in Step 2 of FIG. 5, the micro-pores 6 are occluded on the syringe device by rotating the micro-pore occluder 7 into place as shown in FIG. 4A, so that the micro-pores are occluded, as shown in FIG. 5B.

Figure 5C:
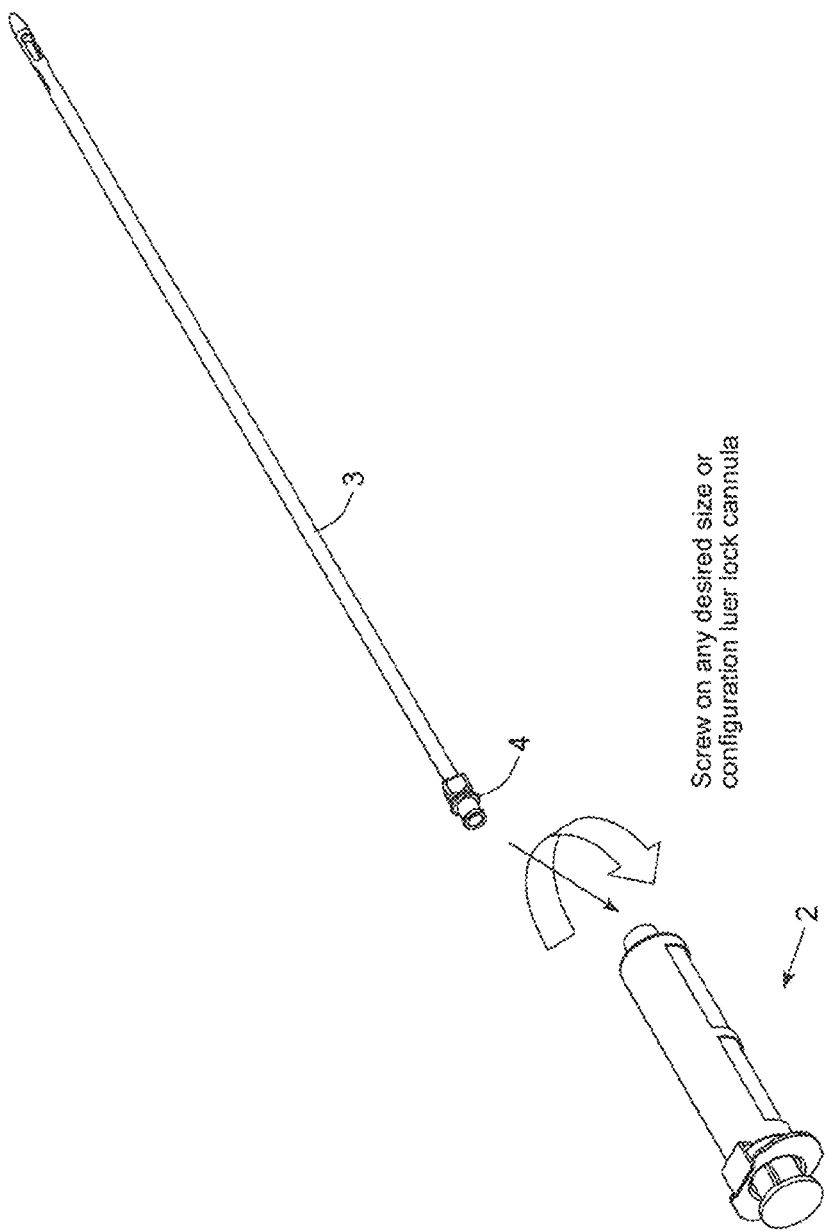
FIG. 5C is a perspective view of the tissue sampling, processing and injection syringe device of FIG. 2, showing a cannula being attached to the distal end opening of the collection barrel.

As indicated in Step 3 of FIG. 5, a suitable cannula is attached to the syringe device 2 as shown in FIG. 5C, and then inserting the cannula 3 into donor site of patient, as shown in FIG. 5D2.

As indicated in Step 4 of FIG. 5, the plunger 8B is withdrawn to create vacuum and collect fat in syringe device, until full, as shown in FIG. 5D1. As the tissue collection tube 5 is made from optically transparent plastic material, the surgeon is able to visually detect the status of tissue filling operations at any moment in time with a simple visual glance at the syringe device.

Optionally, as indicated in Step 5 of FIG. 5, a volume of irrigation solution (e.g. insulin and/or growth factor enrichment solution) is aspirated through the syringe device, containing a collection tissue sample, for the purpose of cleansing and conditioning the tissue sample after harvesting.

Figure 5E:
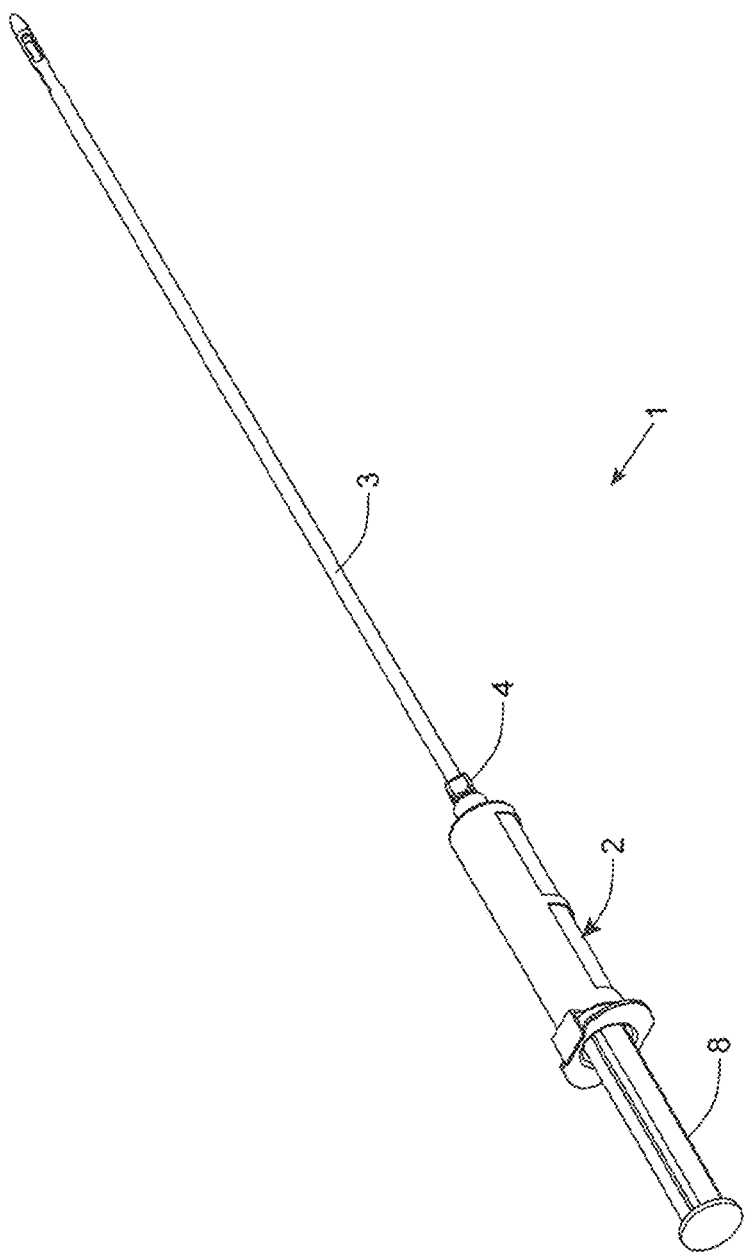
FIG. 5E is a perspective view of the tissue sampling, processing and injection syringe device of FIG. 2, shown filled with fat tissue.

As indicated in Step 6 of FIG. 5, the cannula 3 is removed from patient when the optically transparent tissue collection tube 5 is filled with tissue, as indicated in FIG. 5E.

As indicated in Step 7 of FIG. 5, the cap 12 is attached to the distal end opening (i.e. tip) of the tissue collection tube of the syringe device.

Method of Processing Aspirated Tissue Sample Using the Tissue Sampling, Processing and Injection Syringe Device of the Present Invention The flow chart of FIG. 6 describes the primary steps carried out when practicing the method of processing an aspirated tissue sample using the tissue sampling, processing and injection syringe device of the present invention shown in FIGS. 2 through 4D.

Figure 6A:
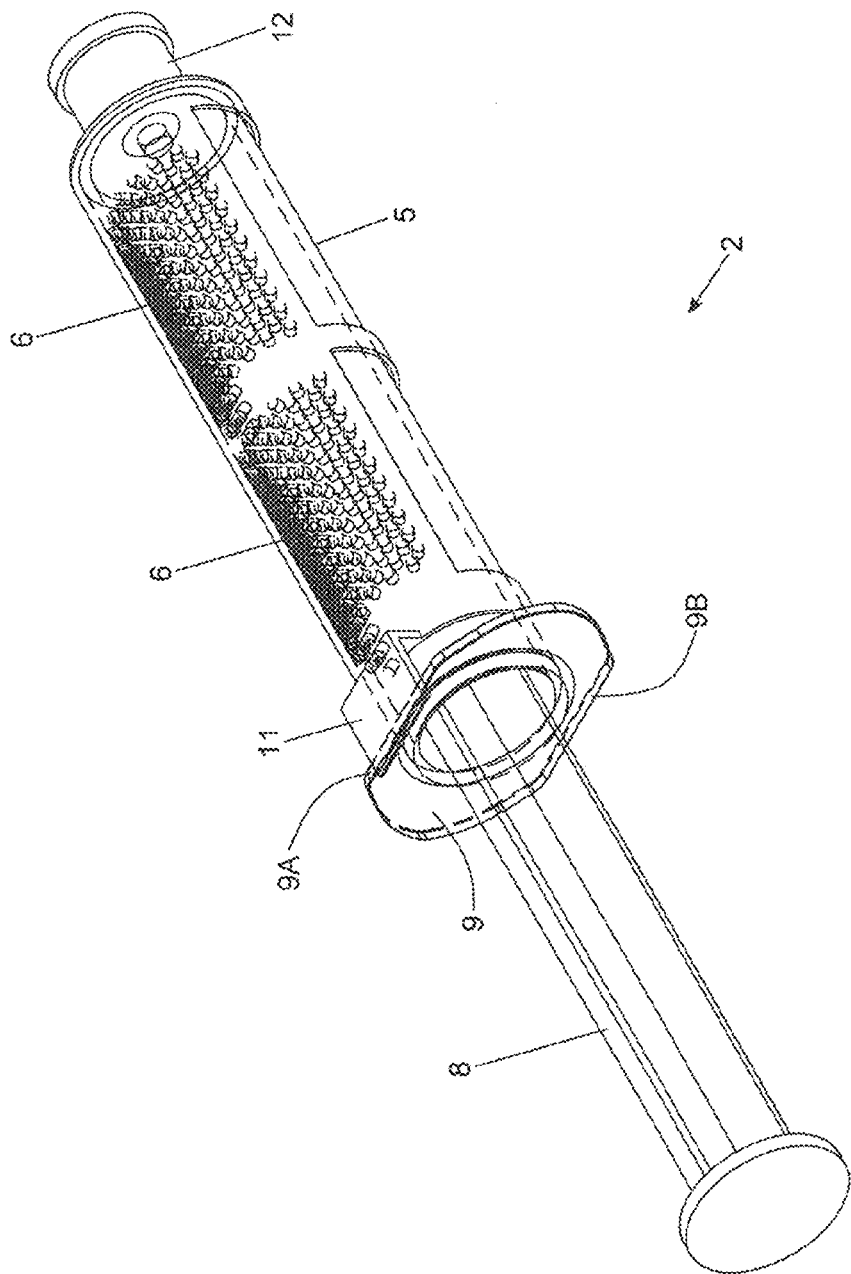
FIG. 6A is a perspective view of the tissue sampling, processing and injection syringe device of FIG. 2, shown with its cannula removed and its distal end opening capped.

As indicated in Step 1 of FIG. 6, the cannula 3 is removed from the distal end portion of the tissue collection tube 4, and a cap 12 is attached to the tip thereof to close off the distal end opening of the tissue collection tube 5, as shown in FIG. 6A. Alternatively, the surgeon's finger can be placed over the distal tip portion, to close off the same, during the following operations described in Steps 2 and 3 below.

As indicated Step 2, the micro-pores of the syringe device are exposed (i.e. configured in the non-occluded state) as shown in FIG. 6B. In this non-occluded state, fluid in a collected tissue sample can be filtered/expressed through the micro-pores 6 of the collection tube 5 when the plunger 8B is manually pushed into the collection tube while the micro-pores are non-occluded to concentrate the collected tissue sample for re-injection into a patient, or subsequent processing at a tissue bank.

Figure 6C:
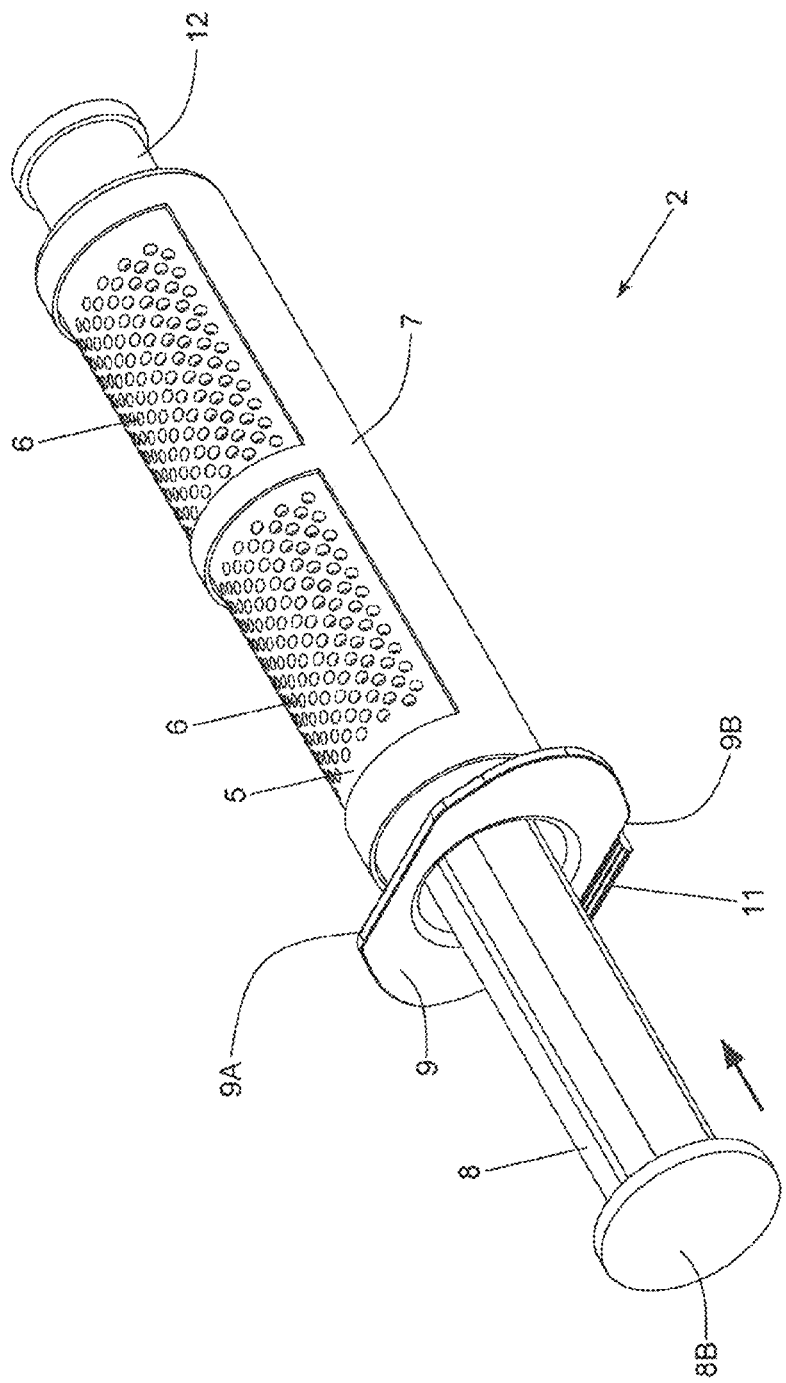
FIG. 6C is a perspective view of the tissue sampling, processing and injection syringe device of FIG. 2, shown being used to concentrate a fat tissue sample within the collection tube by manually pushing its plunger into the collection tube while the micro-pores in the collection tube are in a non-occluded state, allowing fluid in the tissue sample to be expressed (i.e. filtered) through the non-occluded micro-pores and the collected tissue sample to be concentrated for re-injection into the patient, or subsequent processing at a tissue bank.
Figure 6D:
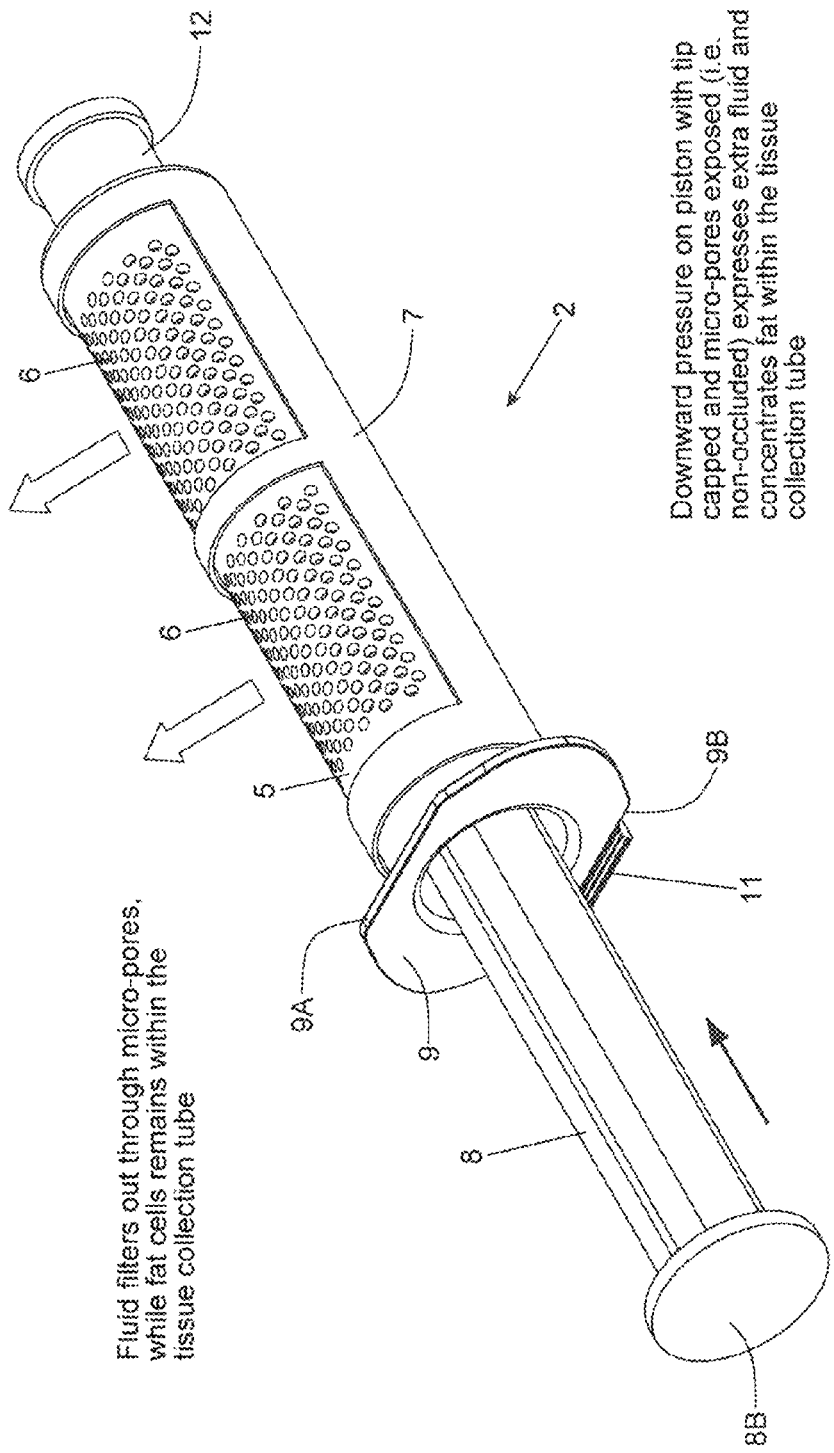
FIG. 6D is perspective view of the tissue sampling, processing and injection syringe device of the present invention, showing its plunger being manually pushed into the collection tube while the micro-pores in the collection tube are in a non-occluded state, allowing fluid in the tissue sample to be expressed through the non-occluded micro-pores and the collected tissue sample to be concentrated for rejection into the patient or subsequent processing at a tissue bank.

As indicated in Step 3, the surgeon gently depresses the piston's plunger 8B to express extra fluid from the collected tissue sample, is expressed through the non-occluded micro-pores 6 and the collected tissue sample is concentrated (in terms of cellular content) as shown in FIGS. 6C, and 6D, for rejection into the patient or subsequent processing at a tissue bank.

As in Step 4, the micro-pores on the tissue collection tube are then occluded by manually rotating the micro-pore occluder 7 into its micro-pore occlusion state, as illustrated in FIG. 6B. In this occluded state, the sample of concentrated tissue can be ejected from the collection tube 5 when the plunger 8B is pushed into the collection tube while the micro-pores 6 are occluded.

Method of Injecting a Processed Tissue Sample into a Patient Using a Filled Tissue Sampling, Processing and Injection Syringe Device of the Present Invention The flow chart of FIG. 7 describes the steps involved when carrying out the method of injecting a processed tissue sample into a patient using a filled tissue sampling, processing and injection syringe device of the present invention.

As indicated in Step 1 of FIG. 7, the tip cover 12 is removed from the syringe device 2.

As indicated in Step 2, the micro-pores 6 on the tissue collection tube are occluded by rotating the micro-pore occluder 7 to the micro-pore occlusion state, shown in FIG. 4B.

Figure 7A:
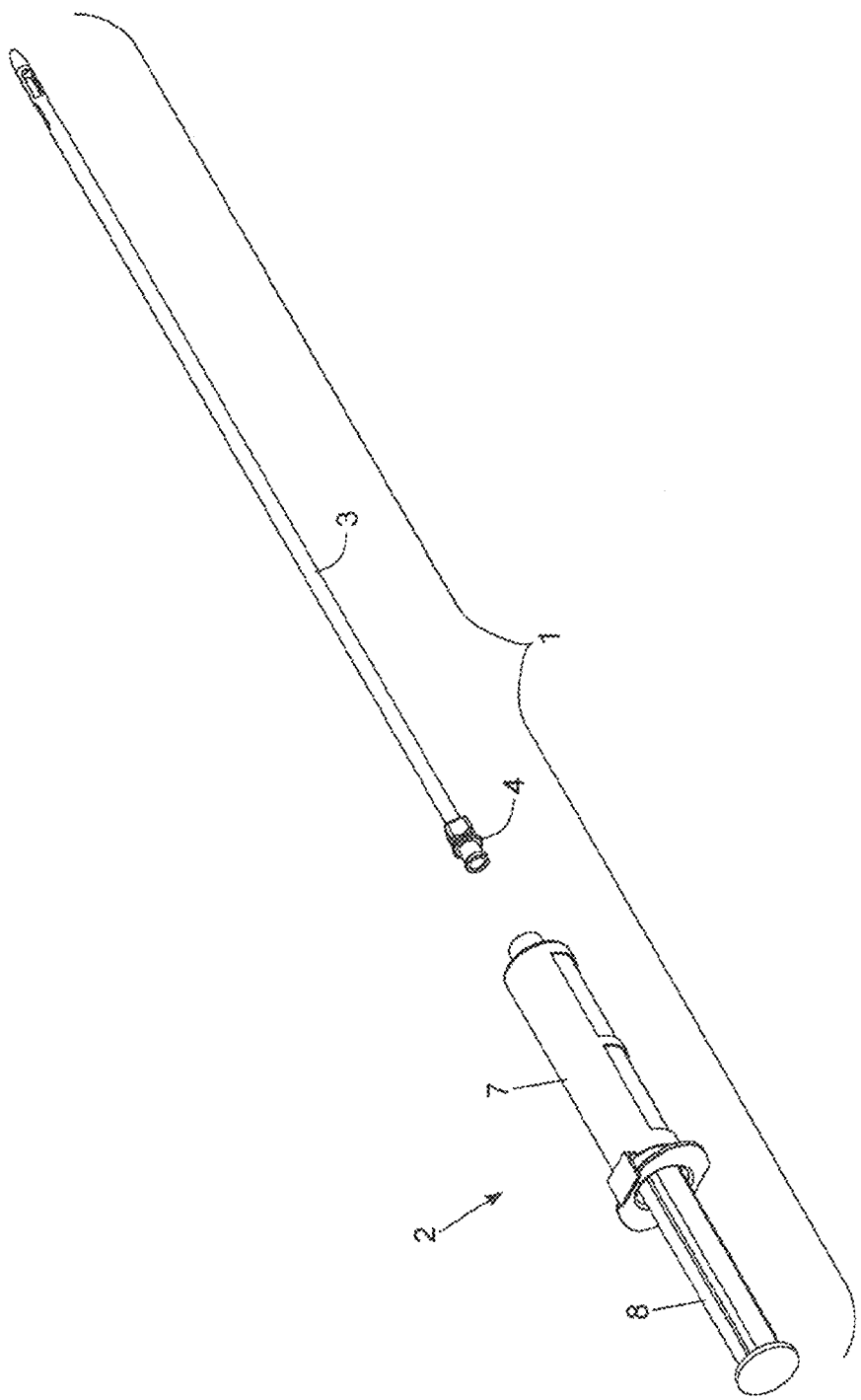
FIG. 7A is a perspective view of the tissue sampling, processing and injection syringe device of the present invention, showing a cannula being installed on its distal end opening, connected using a Leur lock connector.
Figure 7B:
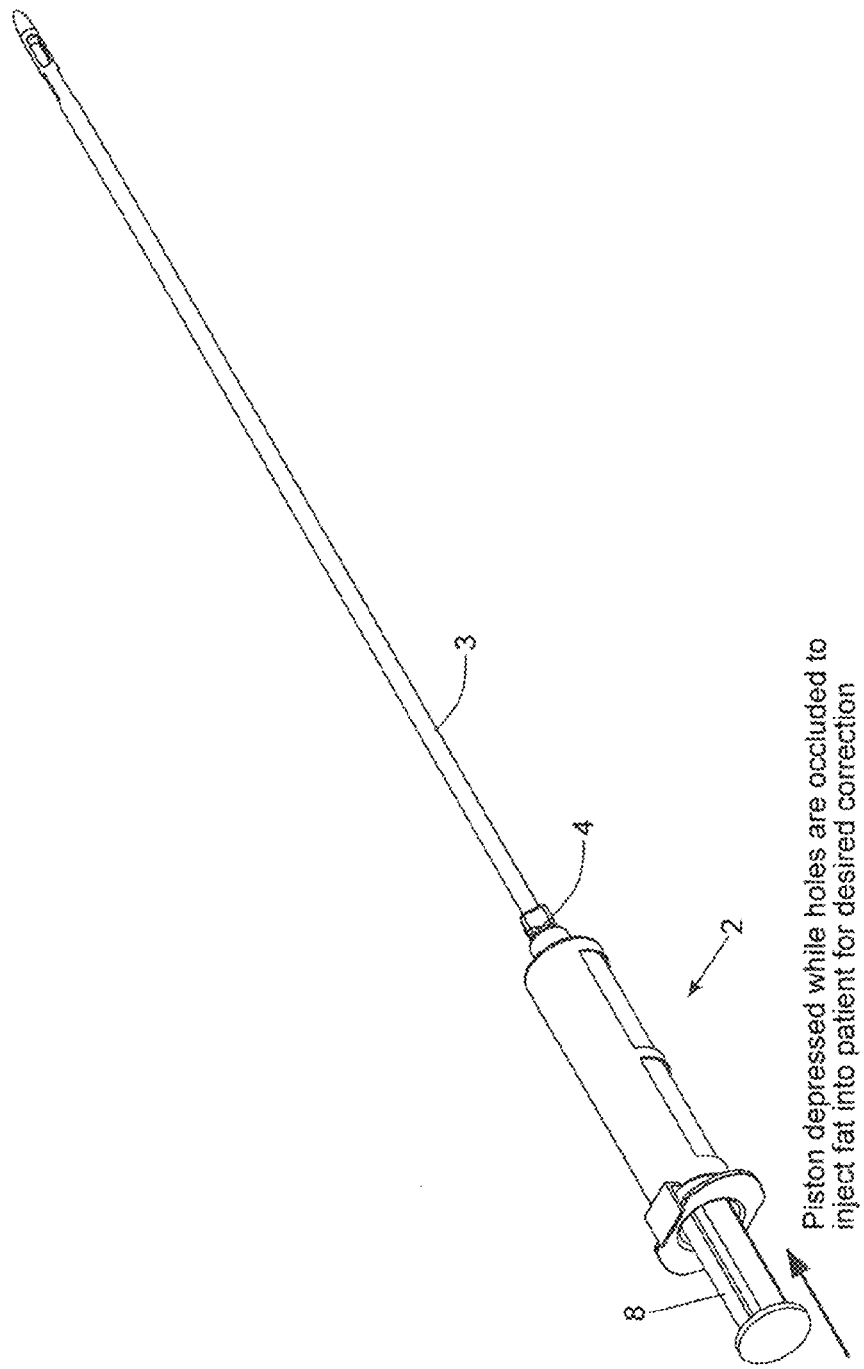
FIG. 7B is a perspective view of the tissue sampling, processing and injection syringe device of the present invention, shown configured for injecting fat tissue sample into a patient, by depressing the plunger piston while the micro-pores are arranged in the occluded state.
Figure 7C:
FIG. 7C is a perspective view of a patient having a tissue sample injected beneath her skin a surgeon using the tissue sampling, processing and injection syringe device of the present invention.
Figure 7D:
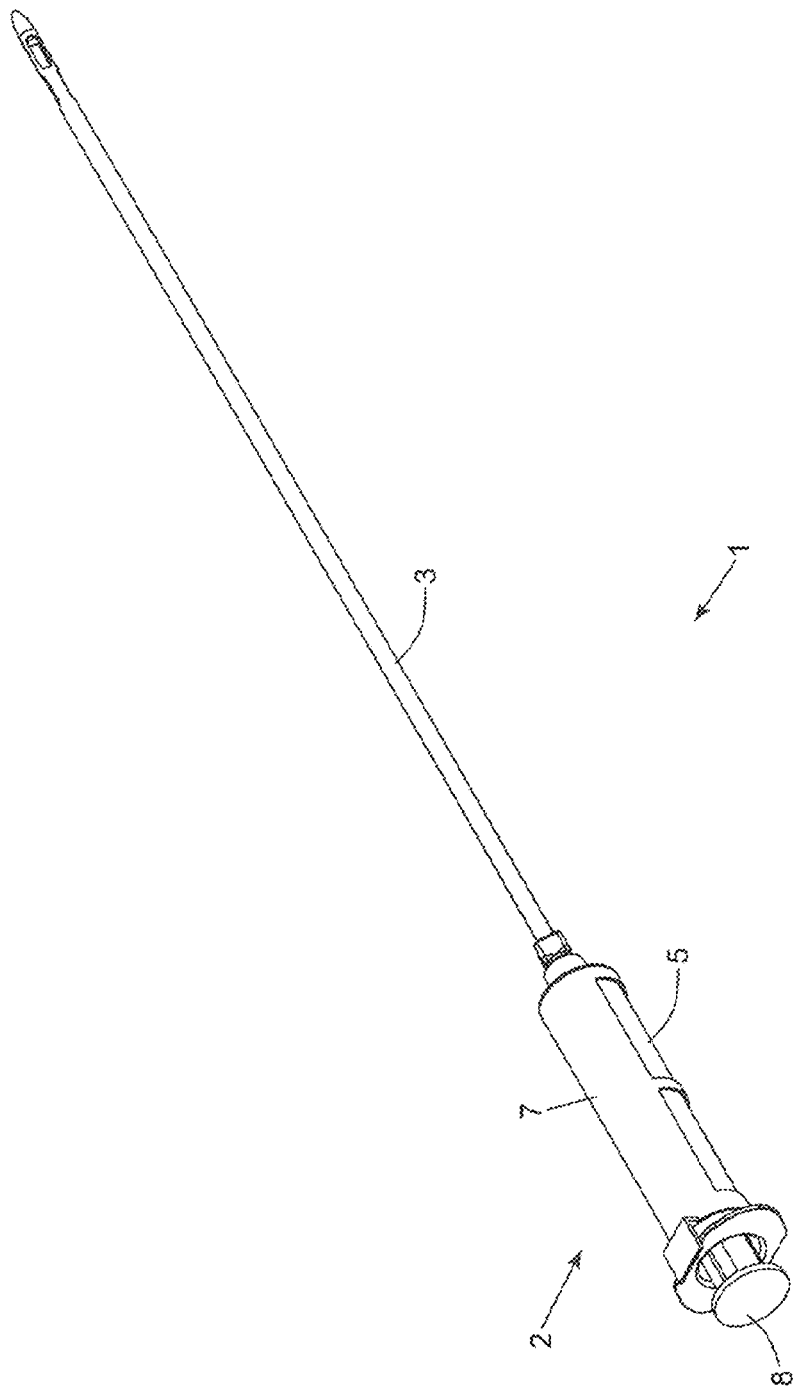
FIG. 7D is a perspective view of the tissue sampling, processing and injection syringe device of the present invention, shown configured in a state after the surgeon completes the injection of the fat tissue sample into the patient.

As indicated in Step 3, a cannula 3 is attached to the distal end opening of the tissue collection tube 5, as shown in FIG. 7A, and then inserted into a patient where correction is required, by depressing plunger's piston 8B to inject fat into the patient as required, as shown in FIGS. 7B and 7C.

Optionally, as indicated in Step 4, the tissue sample material can be ejected out of the tissue collection tube of the syringe device 2, and into an empty (no air) plastic bag for the purpose of delivering tissue material to tissue bank.

Method of Harvesting, Processing and Injecting a Tissue Sample into a Patient Using the Tissue Sampling, Processing and Injection Syringe Device of the Present Invention The flow chart of FIG. 8 describes the primary steps carried out when practicing the method of harvesting, processing and re-injecting a tissue sample into a patient using the tissue sampling, processing and injection syringe device of the present invention, depicted in FIGS. 1 through 7D. These steps are a compilation of the steps previously described in the flow charts of FIGS. 5, 6 and 7, and will not be repeated here for sake of brevity.

Specification of the In-Line Three-Pack Tissue Sampling, Processing and Collection Device of the Present Invention The flow chart of FIG. 9 describes the primary steps carried out when practicing the method of harvesting tissue samples from a patient using the 3-pack tissue sampling, processing and collection device of the present invention, shown in FIGS. 9A, 9B and 9C, while connected in-line with hand-held power-assisted tissue aspiration instrument 10 as disclosed in Applicant's copending U.S. application Ser.

Nos. 12/850,786, 12/462,596 and 12/813,067, incorporated herein by reference incorporated herein by reference. However, before describing this method in detail, it is appropriate to describe the 3-pack tissue sampling, processing and collection device of the present invention, shown in FIGS. 9A, 9B and 9C.

As shown in FIG. 9A, the 3-pack tissue sampling, processing and collection device 30 comprises: an optically-transparent collection chamber 31 having closed end 31A with a central aperture 32, and an open end 31B with hollow inner chamber/space 31C disposed between the closed end 31A and the open end 31B; a removable lid 33 for threaded connection to the open end of the collection chamber, and having a central flow channel 34 terminated in a first barbed connector 35 for connecting the device to vacuum source 36 by way of a section of flexible vacuum tubing 37; a stationary suction plate 38 having three hollow projections 39A through 39C for supporting the open ends of three tissue collection tubes (i.e. syringe barrels) 5A through 5C, each having micro-pores or perforations 6 formed in the walls thereof (to allow fluid to flow and filter therethrough while in the collection chamber) and being keyed for registration with the collection chamber (to prevent rotation); and a second connector 40 connected by threads to the hollow selector post 32 allowing the 3-pack tissue sampling, processing and collection device 30 to be directly connected to the hand-held power-assisted tissue aspiration instrument 10, indirectly by way of a second section of flexible vacuum tubing 41, as may be desired by the surgeon. These components are assembled as shown in FIGS. 9C and 9D.

As indicated in Step 1 of FIG. 9, the barbed connector 35 on back of hand-held tissue aspiration instrument 10 is removed, preparing the device for connection in-line with a hand-held power-assisted tissue aspiration instrument.

As indicated in Step 2 of FIG. 9, the 3-pack tissue sampling, processing and collection device 30 is attached (i.e. by threads) to the outlet port of the hand piece portion of a powered tissue aspiration instrument 10, as described above.

As indicated Step 3, the barb connector removed from the hand-held tissue aspiration instrument is attached to the rear portion of the 3-pack tissue sampling, processing and collection device, to allow for the connection of flexible tubing between the 3-pack tissue sampling, processing and collection device 30 and a vacuum source 36, as shown in FIG. 9C. Preferably, the collection chamber 31 is labeled for orientation, indicating the side to patient and the side to vacuum source. Also, the suction plate 38 has numbers 1 through 3 for each of the capped (i.e. stoppered) tissue collection tubes (i.e. syringe barrels) 5A through 5C connected to the suction plate 38 and contained within the collection chamber 31

As indicated in Step 4, the selected area is irrigated with fluid during tissue aspiration, as desired, as shown in FIG. 9D.

As indicated in Step 5, fat tissue is aspirated from the patient as shown in FIG. 9D, until the three (3) tissue collection tubes 5A through 5C within the collection chamber 31 are filled with fat tissue. As the collection chamber and tissue collection tubes are all made from optically transparent plastic material, the surgeon is able to visually detect the status of tissue filling operations at any moment in time with a simple visual glance at the tissue sampling, processing and collection device.

As shown in FIG. 9E, during tissue aspiration operations using the 3-pack tissue sampling, processing and collection device, aspirated fat tissue flows from the sampled region of the patient, through the hand-held tissue aspiration instrument 10 through tubing 41 and the hollow post 32, through passageway/flow 43, into the tissue collection tubes 5A through 5C supported on the stationary suction plate 38 and capped with cap portions 12A through 12C, respectively. Fat cells are concentrated within the tissue collection tubes while excess fluid is expressed and filtered through micropores 6 formed in the side walls of the tissue collection tubes, and passed out through the barded connector 35 towards to vacuum source 36, in a conventional manner. This process, occurring within the 3-pack device, leaves concentrated tissue samples in the tissue collection tubes, prepared for reinjection into the body of the donor patient, or other patient requiring tissue injection.

Optionally, as indicated in Step 6, a volume of irrigation solution is aspirated through the tissue sampling, processing and collection device so as to lavage (i.e. cleanse or wash) the tissue samples contained in the tissue connection tubes, while still contained within the device. This will facilitate further filtration and concentration of the cellular materials within the tissue collection tubes.

Method of Processing Aspirated Tissue During Harvesting Using the 3-Pack Tissue Sampling, Processing and Collection Device of the Present Invention, Coupled in-Line to a Hand-Held Powered Tissue Aspiration Instrument The flow chart of FIG. 10 describes the steps carried out when practicing the method of processing aspirated tissue during harvesting using the 3-pack tissue sampling, processing and collection device of the present invention 30, coupled in-line to a hand-held powered tissue aspiration instrument 10, described above.

As indicated in Step 1, the processing (i.e. filtration, cleansing and concentration) of tissue samples contained within the tissue collection tubes 5A through 5C, occurs automatically during tissue aspiration and collection operations. Such processes have been detailed in Steps 4, 5 and 6 in the method described in FIG. 9, above.

As indicated in Step 2, the vacuum tubing is removed from the 3-pack tissue sampling, processing and collection device 30.

As indicated in Step 3, the 3-pack tissue sampling, processing and collection device 30 is disconnected from hand piece portion of the hand-held power tissue aspiration instrument 10, by way of an unscrewing action of the 3-pack device 30 relative to the hand piece portion of the hand-held power-assisted tissue aspiration instrument 10.

As indicated in Step 4, the barbed connector 35 is replaced on back of hand piece of the tissue aspiration instrument 10, as shown in FIG. 10A.

As indicated in Step 5, the lid on the 3-pack tissue sampling, processing and collection device 30 is removed, as shown in FIG. 10B, revealing the fat-filled tissue collection tubes 5A through 5C mounted on the suction plate 38.

As indicated in Step 6, the fat-filled tissue collection tubes 5A through 5C are removed from the collection chamber 41, as shown in FIG. 10C, with the capped distal tips of the collection tubes facing downwardly.

As indicated in Step 7, a plunger and piston subassembly 8 is inserted into the proximal end opening of each capped tissue collection tube, and returned to the surgeon for immediate reinjection into the patient.

Optionally, as indicated in Step 7, the tissue filled injection syringes, completed in Step 7, can be delivered, plunger up, to a tissue banking facility, where a musculoskeletal stem cell line or hematopoietic line can be grown out to recoup a stem cell enriched culture of cells that may be returned to the surgeon for auto-graft into the patient, with adipose cell markers, ideal for facial rejuvenation.

Method of Injecting Processed Tissue Samples into a Patient Using a Fat-Filled Tissue Injection Syringe Device of Present Invention The flow chart of FIG. 11 describes the primary steps carried out when practicing the method of injecting processed tissue samples into a patient using a fat-filled tissue injection syringe device of present invention, constructed by attaching a flanged micro-pore occluder onto a fat-filled tissue collection tube and inserting a plunger and piston into the proximal end opening of the tissue collection tube, as described below.

As indicated in Step 1, the distal tip cap is removed from the fat-filled tissue collection tube.

As indicated in Step 2, a micro-pore occluder 7 is slid over the tissue collection tube 5 so as to cover the micro-pores 6, and snap flange 11 in place, to form a tissue injection syringe device 2, as shown in FIGS. 3B and 4A.

Figure 11A:
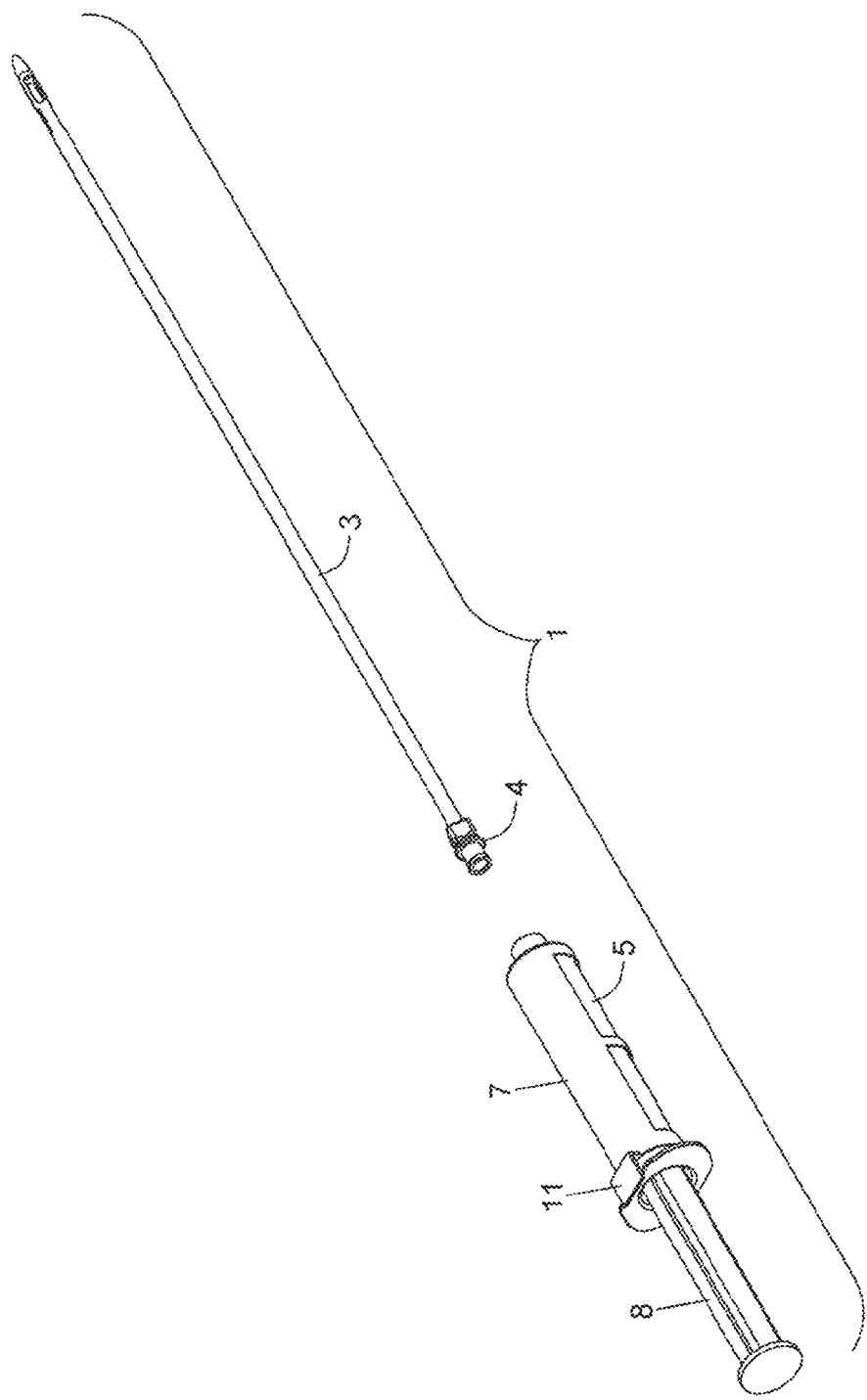
FIG. 11A is a perspective view of a fat-filled tissue injection syringe device of present invention, constructed by attaching a micro-pore occluder to a fat-filled collection tube removed from the dissembled 3-pack tissue sampling, processing and collection device of FIG. 10C to occlude its micro-pores, and then inserting a plunger and piston into the proximal end opening of the collection tube (i.e. barrel), and finally attaching a cannula to the distal end opening of the collection tube, by way of a Leur locking connector assembly.

As indicated in Step 3, a luer lock cannula 3 is screwed onto the distal tip portion of the tissue injection syringe device 2 for reinjection of harvested and processed tissue sample, as shown in FIG. 11A.

As indicated in Step 4, the cannula 3 is the inserted into the patient in the area of correction, as shown in FIG. 11C.

Figure 11B:
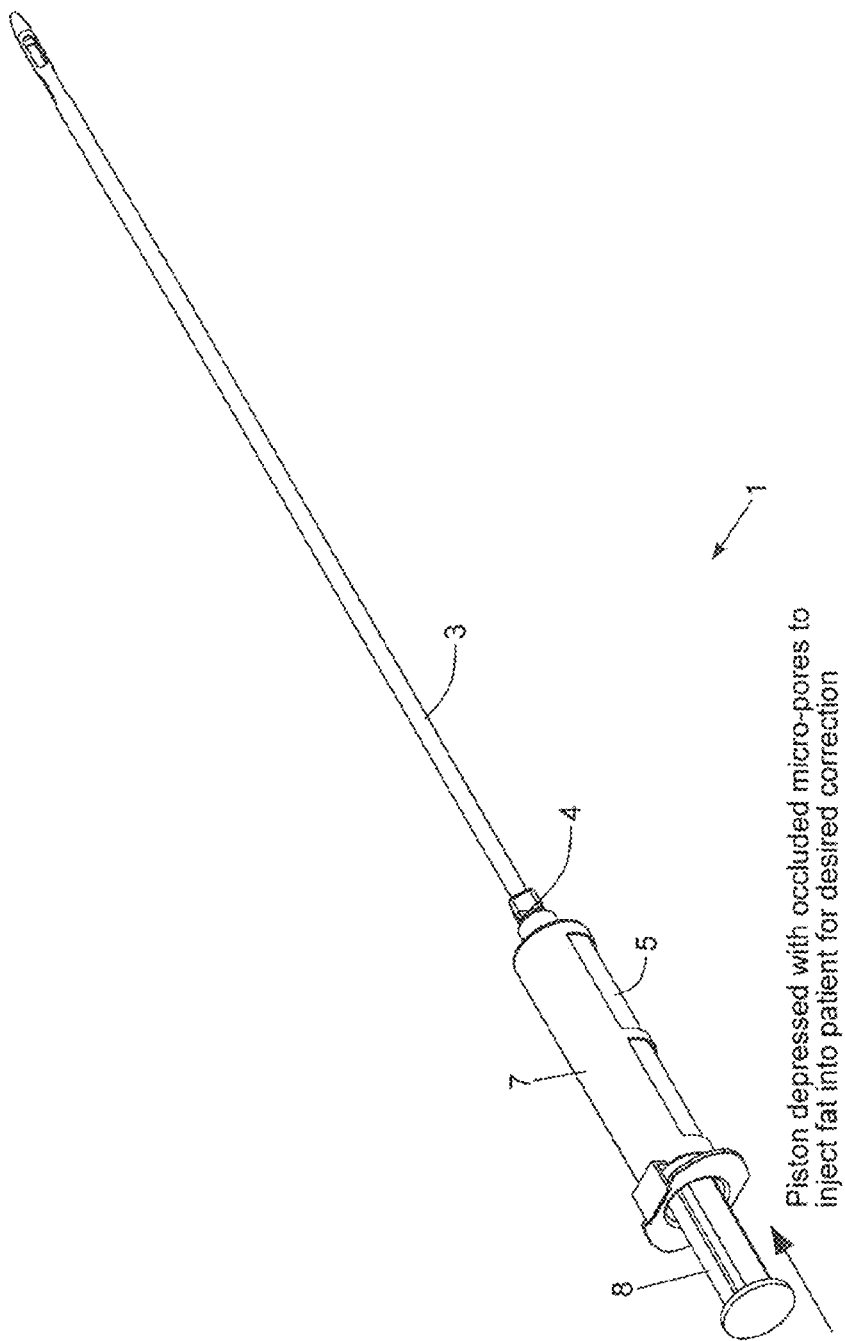
FIG. 11B is a perspective view of the fat-filled tissue injection syringe device of present invention constructed in FIG. 11A, shown being used by a surgeon to inject tissue into a patient by depressing the piston into the collection tube while its micro-pores are in their occluded state.

As indicated in Step 5, plunger's piston 8B is gently depressed into the tissue collection tube (i.e. syringe barrel) 5 as shown in FIG. 11B, to inject sufficient tissue into the patient to obtain the desired correction.

Figure 11D:
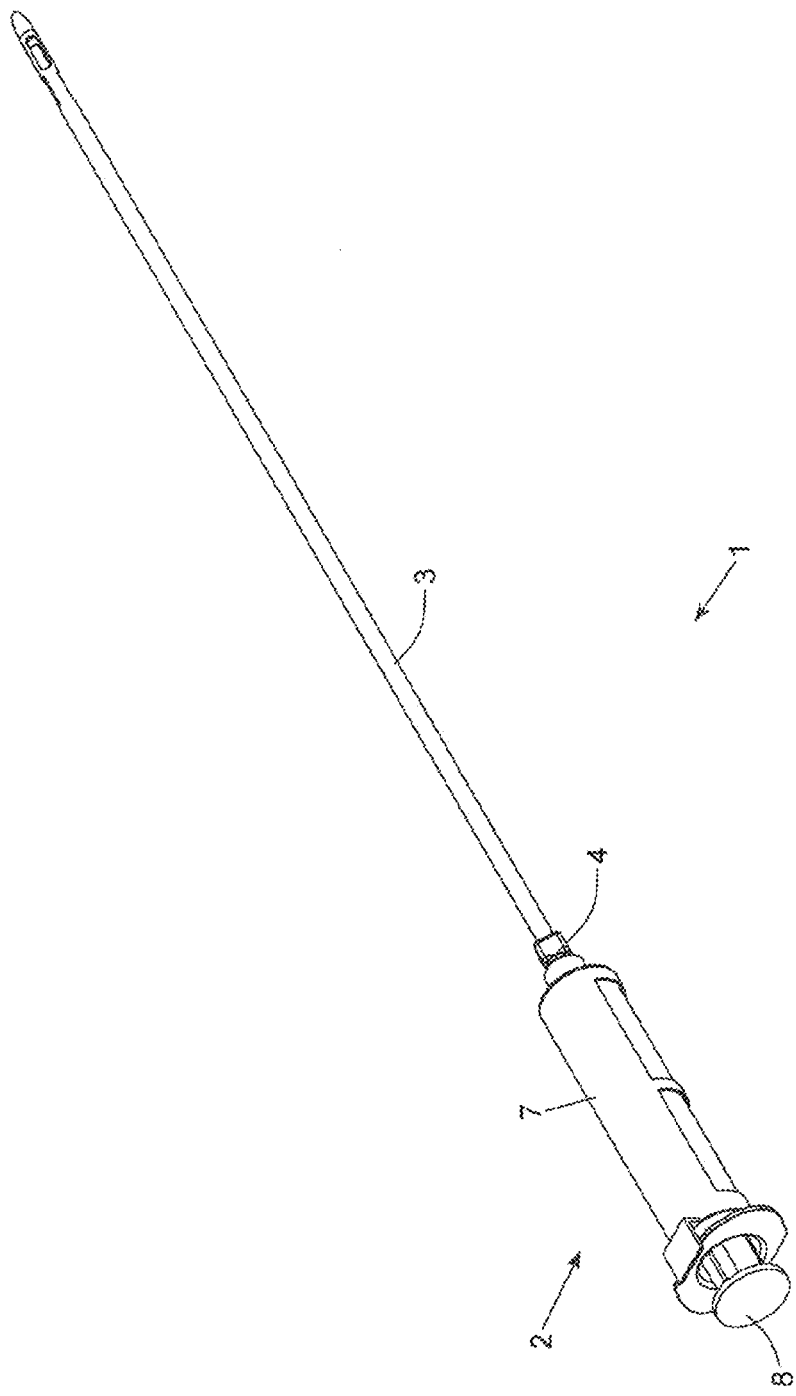
FIG. 11D is a perspective view of the tissue injection syringe device of FIG. 11D after it has been emptied of its tissue sample.

When all tissue has been emptied from the syringe device 2, it will be configured as shown in FIG. 11D.

Method of Harvesting, Processing and Injecting a Tissue Sample into a Patient Using the Tissue Sampling, Processing and Injection Syringe Device of the Present Invention The flow chart of FIG. 12 describes the primary steps carried out when practicing the method of harvesting, processing and injecting a tissue sample into a patient using the tissue sampling, processing and injection syringe device of the present invention, depicted in FIGS. 9 through 11D. As these steps are a compilation of the steps previously described in the flow charts of FIGS. 9, 10 and 11, they will not be repeated here for sake of brevity.

Specification of the In-Line Six-Pack Tissue Sampling, Processing and Collection Device of the Present Invention The flow chart of FIG. 13 describes the primary steps carried out when practicing the method of harvesting tissue samples from a patient using the 6-pack tissue sampling, processing and collection device of the present invention 60, shown in FIGS. 13A through 13E, while connected in-line with hand-held power-assisted tissue aspiration instrument 10 as disclosed in Applicant's copending U.S. application Ser. Nos. 12/850,786, 12/462,596 and 12/813,067, incorporated herein by reference incorporated herein by reference. However, before describing this method in detail, it is appropriate to describe the 6-pack tissue sampling, processing and collection device of the present invention, shown in FIGS. 13A through 13E.

As shown in FIG. 13A, the 3-pack tissue sampling, processing and collection device 60 comprises: an optically-transparent collection chamber 61 having closed end 61A with a central aperture 62, and an open end 61B with hollow inner chamber/space disposed 61C between the closed end 61A and the open end 61B; a removable lid 63 for threaded connection to the open end of the collection chamber, and having a central flow channel 64 terminated in a first barbed connector 65 for connecting the device to vacuum source 36 by way of a section of flexible vacuum tubing 37; a stationary suction plate 68 having six hollow projections 69A through 69H for supporting the open proximal ends of six tissue collection tubes (i.e. syringe barrels) 5A through 5H respectively, each having micro-pores (i.e. perforations) 6A, 6B formed in the side walls thereof (to allow fluid to flow and filter therethrough while in the collection chamber), capped with caps 12A through 12H, and being keyed for registration with the collection chamber 61 (to prevent rotation); a rotatable selector 70, shown in FIG. 13A, for rotational engagement with the suction plate 68 and having a hollow central post section 71 that passes through central aperture 62 and establishes fluid communication with a passage/conduit 72 that extends from center of the to periphery to control the flow of aspirated fat sample from the instrument 10 through the first section of tubing 79, through the selector 70 and into the selected collection tube/projection 69/5 combination; a turning knob 75 mounted on and engaging with the hollow selector post 71 and enabling the turning of the rotatable selector 70 relative to the stationary suction plate 68 to select the collection tube/projection combination (5/69) into which an aspirated fat sample should flow for collection and indexing purposes during tissue sampling; a spring 76 mounted between the turning knob 75 and hollow selector post 71 to push up the turning knob and keeping the selector 70 at the bottom of the collection chamber 71; and a second barbed connector 77 connected by threads to the hollow selector post 71 allowing the tissue sampling, processing and collection device 60 to be connected to the hand-held tissue aspiration instrument 10 by way of a second section of flexible vacuum tubing 79.

Surgeon installs the tissue sampling, processing and collection device 60 inline between the fat aspiration instrument 10 and the vacuum source 36 as shown in FIG. 13F. The collection chamber 61 is labeled for orientation, indicating the side to patient and the side to vacuum source. The turning knob 75 has an arrow on it. The suction plate 69 has numbers 1-6 for each of the capped and perforated tissue collection tubes (i.e. syringe barrels) 5A through 5H mounted on the projections of the suction plate 68. The surgeon then pushes down on turning knob 75 against the biasing force of spring 76 and that pushes the selector 70 slightly forward so the knob 75 can be turned to select which tissue collection tube (i.e. syringe barrel) 5A through 5H to collect to, until it is full, counting from 1 to six. The selector 70 has a passageway/flow director 80 which extends to the selected tissue collection tube to complete the fluid communication channel, set up by the selector and director, as shown in FIG. 13E. The spring 76 maintains the selector 70 in its selected position. As shown in FIGS. 13C and 13D, suction plate 68 has two flanges 68A and 68B which snap over the selector 70, and grip a groove 70A that runs around it to secure it in place relative to the selector 70, as shown in FIG. 13E.

Figure 13G:
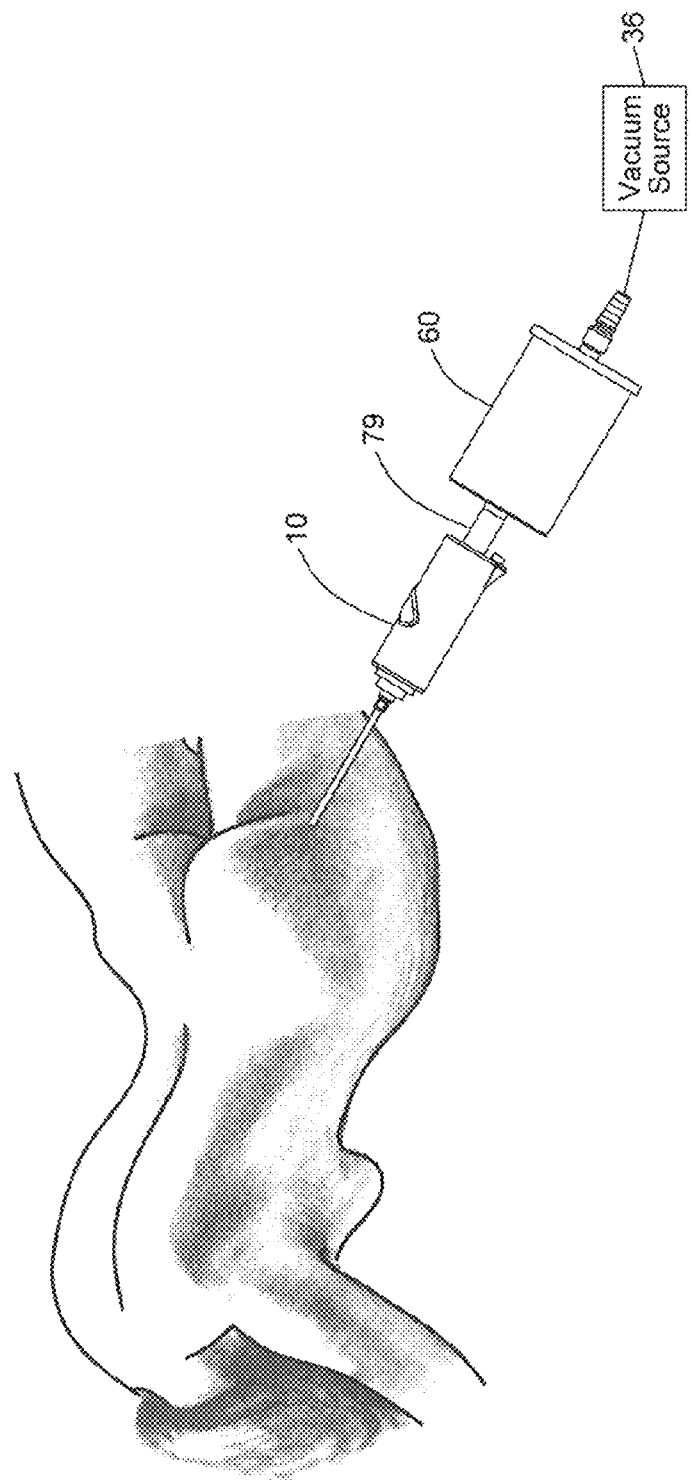
FIG. 13G is perspective view of the six-pack tissue sampling, processing and collection device and hand-held power-assisted tissue aspiration instrument shown in FIG. 13F, being used to aspirate tissue samples from a patient.
Figure 13H:
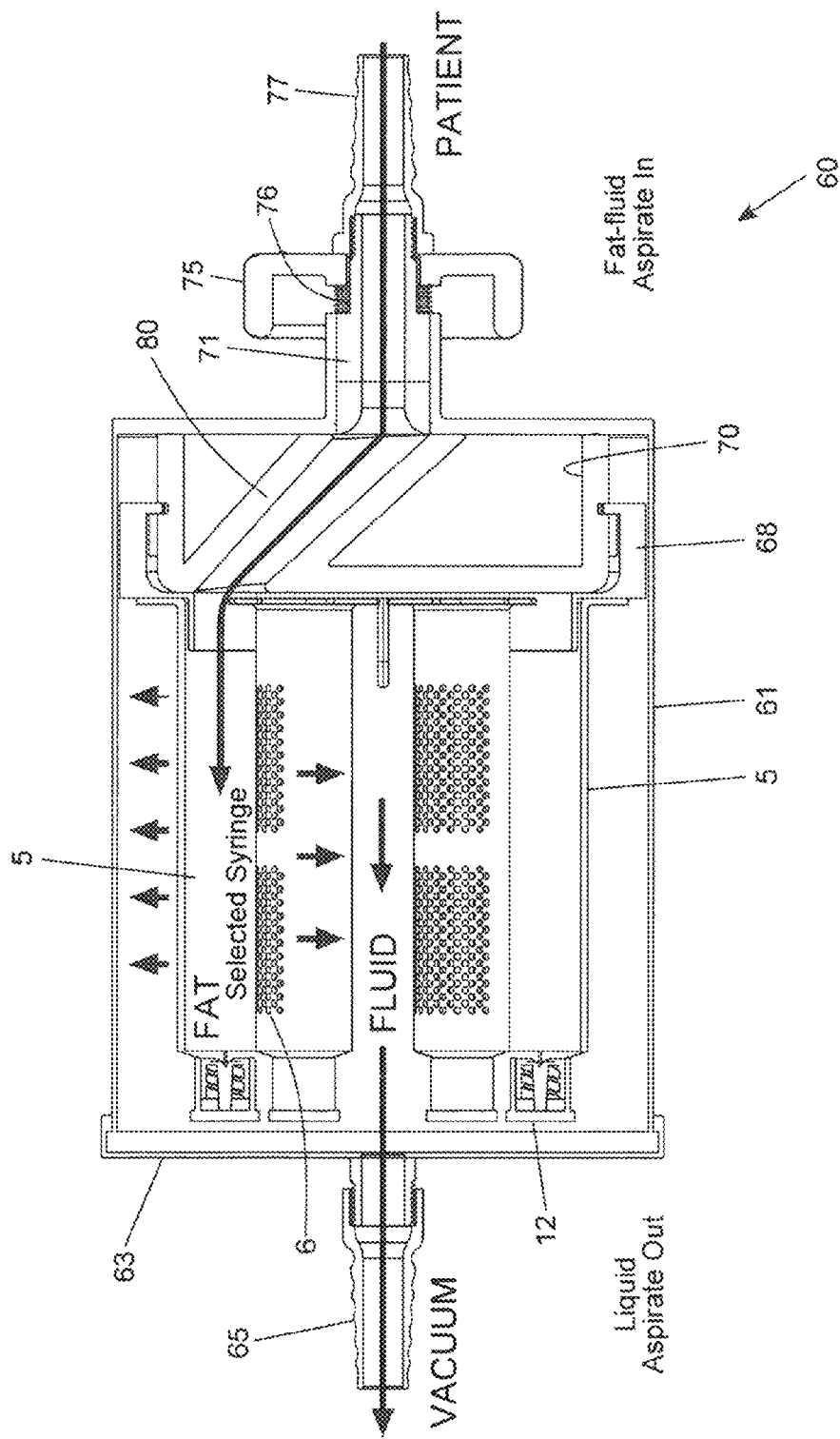
FIG. 13H is a cross-sectional view of the in-line tissue sampling, processing and collection device shown in FIG. 13G, illustrating the flow of an aspirated tissue sample from the patient, through the fat aspiration instrument, to the selector component of the tissue sampling, processing and collection device, through the passageway/flow director, into the selected tissue collection tube, whereupon fat cells are collected within the selected collection tube while excess fluid (i.e. serum and tumescent solution) is expressed through micro-pores (i.e. perforations or fine holes) in the selected tissue collection tube, and passed out through the barded connector towards to vacuum source, leaving cellular components behind because concentrated adipocytes and stem cells are too big to pass through micro-pores and remain within collection tube.

As shown in FIG. 13H, during tissue aspiration operations using the system of the present invention, an aspirated fat sample flows from the sampled region of the patient, through the hand-held tissue aspiration instrument 10, through tubing 79 and the hollow selector post 71, through passageway/flow director 80, into the selected collection tube (i.e. syringe) 5A through 5H supported on the stationary suction plate 68 and capped with cap portion 12A and 12H, respectively. Fat cells are collected within the selected tissue collection tube (i.e. syringe barrel) 5A through 5H, while excess fluid is expressed through micro-pores 6A, 6B formed in the selected collection tube, and passed out through the barded connector 65 towards to vacuum source 36.

Having described the 6-pack tissue sampling, processing and collection device of the present invention above, it is appropriate at this juncture to described how it can be used in tissue sampling, processing and collection operations carried out in accordance with the principles of the present invention.

As indicated in Step 1, the 6-pack tissue sampling, processing and collection device 60 is inserted (i.e. installed) between the hand piece of the hand-held tissue aspiration instrument 10 and the vacuum source 36, as shown in FIG. 13F. Notably, the 6-pack tissue sampling, processing and collection device 60 has six separate tissue collection tubes (i.e. chambers) which may be independently selected by the surgeon, and filled with tissue or aspirate from different areas within a patient during tissue sampling operations. To do so, the surgeon simply turns the selector knob 75 to control the passage of aspirated tissue into the selected tissue collection tube 5A through 5H, providing an unprecedented level of control over tissue sampling operations.

As indicated in Step 2, the aspiration area is irrigated as desired, as shown in FIG. 13G.

As indicated in Step 3, fat tissue is aspirated from the irrigated area in the patient, as shown in FIG. 13G, until the six tissue collection tubes contained in its collection chamber 61 are filled with aspirated fat tissue. As the collection chamber 61 and tissue collection tubes 5A through 5H are all made from optically transparent plastic material, the surgeon is able to visually detect the status of tissue filling operations at any moment in time with a simple visual glance at the tissue sampling, processing and collection device 60.

Optionally, as indicated in Step 4, a volume of irrigation solution can be aspirated from patient, in the sampling region, to lavage (i.e. clean and filter) the tissue samples contained in the tissue collection tubes, after harvesting, processing and collection.

FIG. 13H clearly shows the flow path of the fluid and cellular components of aspirated tissue through the 6-pack tissue sampling, processing and collection device 60 during tissue aspiration and processing operations. As shown, aspirated tissue flows from the patient, through the fat aspiration instrument, to the selector component 70 of the tissue sampling, processing and collection device, then through the passageway/flow director 80, into the selected tissue collection tube (i.e. syringe barrel) 5A through 5H, whereupon fat cells are collected within the selected collection tube, while excess fluid (i.e. serum and tumescent solution) is expressed through micro-pores (i.e. holes) 6 in the selected collection tube, and passed out through the barded connector 65 towards to vacuum source 36, thereby leaving cellular components behind because concentrated adipocytes and stem cells are too big to pass through micro-pores 6 and remain within collection tube (i.e. syringe barrel) 5.

Method of Processing Aspirated Tissue During Harvesting Using the Six-Pack Tissue Sampling, Processing and Collection Device of the Present Invention The flow chart of FIG. 14 describes the primary steps carried out when practicing the method of processing aspirated tissue during harvesting using the six-pack tissue sampling, processing and collection device of the present invention, described in detail hereinabove.

As indicated in Step 1, processing (i.e. filtration, cleansing and concentration) of tissue samples contained within the tissue collection tubes 5, occurs automatically during tissue aspiration and collection operations. Such processes have been detailed in Steps 2, 3 and 4 in the method described in FIG. 13, above.

As indicated in Step 2, vacuum tubing 67 is removed from the six-pack tissue sampling, processing and collection device 60.

As indicated in Step 3, six-pack tissue sampling, processing and collection device 60 is then disconnected from hand piece of the hand-held tissue aspiration device 10 (e.g. by an unscrewing operation).

As indicated in Step 4, the barbed connector 65 is replaced on the back of the hand piece of the hand-held tissue aspiration device 10.

As indicated in Step 5, the lid on the 3-pack tissue sampling, processing and collection device 60 is removed, as shown in FIG. 14A, and the tissue collection tubes 5A through 5H mounted on the suction plate removed from collection chamber 61, as shown in FIG. 14B.

As indicated in Step 6, the fat-filled capped tissue collection tubes 5A through 5H are removed from the collection chamber 61, as shown in FIG. 14C, with the capped distal tips of the collection tubes faced downwardly.

As indicated in Step 7, a plunger and piston subassembly 8 is inserted into the proximal end opening of each capped tissue collection tube, and returned to the surgeon for immediate reinjection into the patient.

Optionally, as indicated in Step 7, the tissue filled injection syringes, completed in Step 7, can be delivered, plunger up, to a tissue banking facility, where a musculoskeletal stem cell line or hematopoietic line can be grown out to recoup a stem cell enriched culture of cells that may be returned to the surgeon for auto-graft into the patient, with adipose cell markers, ideal for facial rejuvenation.

Method of Injecting Processed Tissue into a Patient Using a Fat-Filled Tissue Injection Syringe Device of the Present Invention The flow chart of FIG. 15 describes the primary steps carried out when practicing the method of injecting processed tissue samples into a patient using a fat-filled tissue injection syringe device of present invention 2, constructed by attaching a flanged micro-occluder 7 onto the tissue collection tube and inserting a plunger and piston 8 into the proximal end opening of the tissue collection tube, 5A through 5H as described below.

As indicated in Step 1, the distal tip cap 12 is removed from the fat-filled tissue collection tube 5.

As indicated in Step 2, a micro-pore occluder 7 is slid over the tissue collection tube 5 so as to cover the micro-pores 6, and snap the flange 11 in place, to form a tissue injection syringe device 2, as shown in FIGS. 3B and 4A.

Figure 15A:
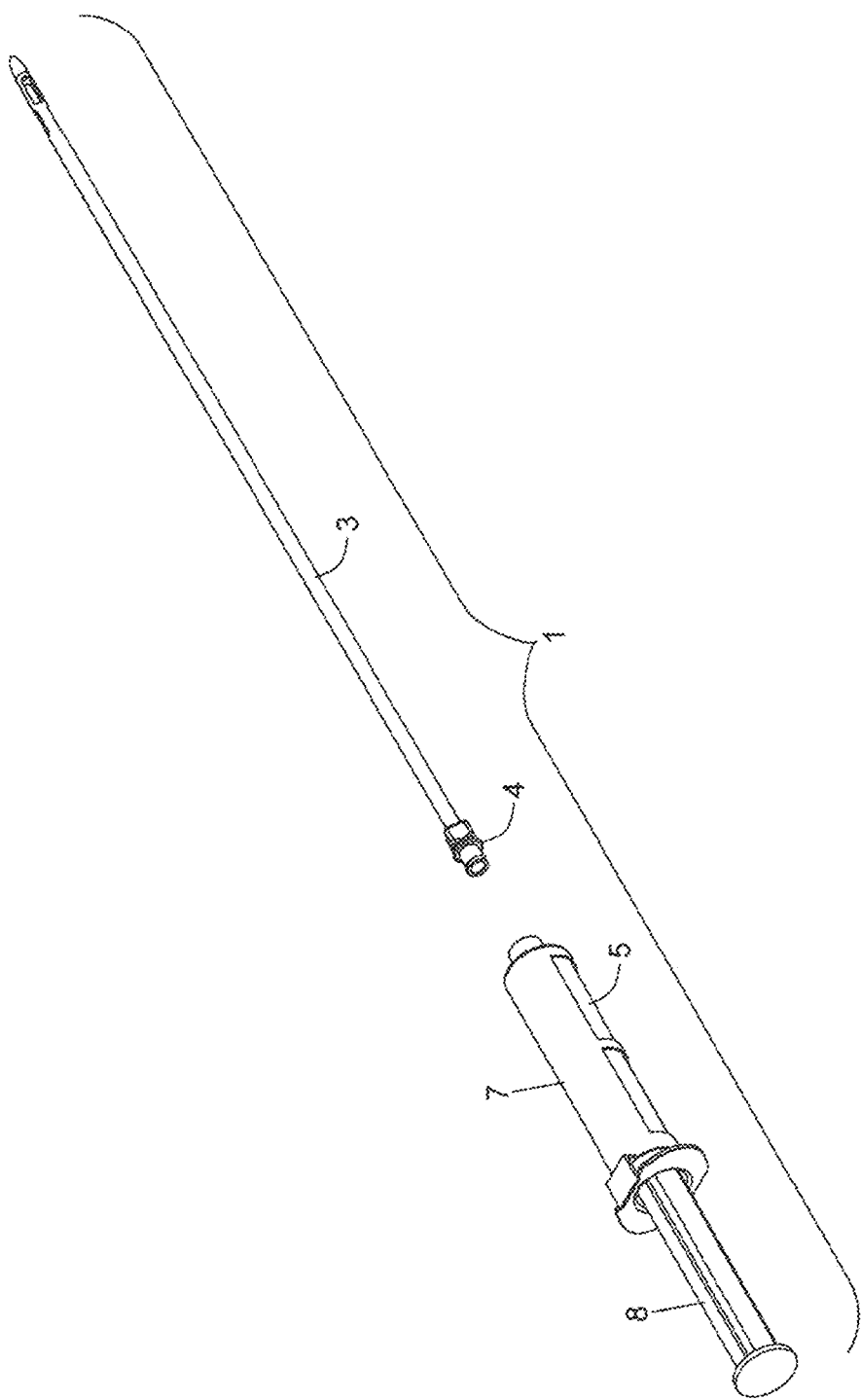
FIG. 15A is a perspective view of a fat-filled tissue injection syringe device of present invention, constructed by attaching a micro-pore occluder to a fat-filled collection tube removed from the dissembled 6-pack tissue sampling, processing and collection device of FIGS. 13A through 13C to occlude its micro-pores, and then inserting a plunger and piston into the proximal end opening of the collection tube (i.e. barrel), and finally attaching a cannula to the distal end opening of the collection tube, by way of a Leur locking connector assembly.

As indicated in Step 3, a luer lock cannula 3 is screwed onto the distal tip portion of the tissue injection syringe device 2 for reinjection of harvested and processed tissue sample, as shown in FIG. 15A.

Figure 15C:
FIG. 15C is a perspective view of the fat-filled tissue injection syringe device of present invention being used to inject processed tissue back into the patient to achieve a desired achieve correction.

As indicated in Step 4, the cannula 3 is the inserted into the patient in the area of correction, as shown in FIG. 15C.

As indicated in Step 5, plunger's piston 8 is gently depressed into the syringe barrel (i.e. tissue collection tube) 5, as shown in FIG. 15B to inject sufficient tissue into the patient to obtain the desired correction.

Figure 15D:
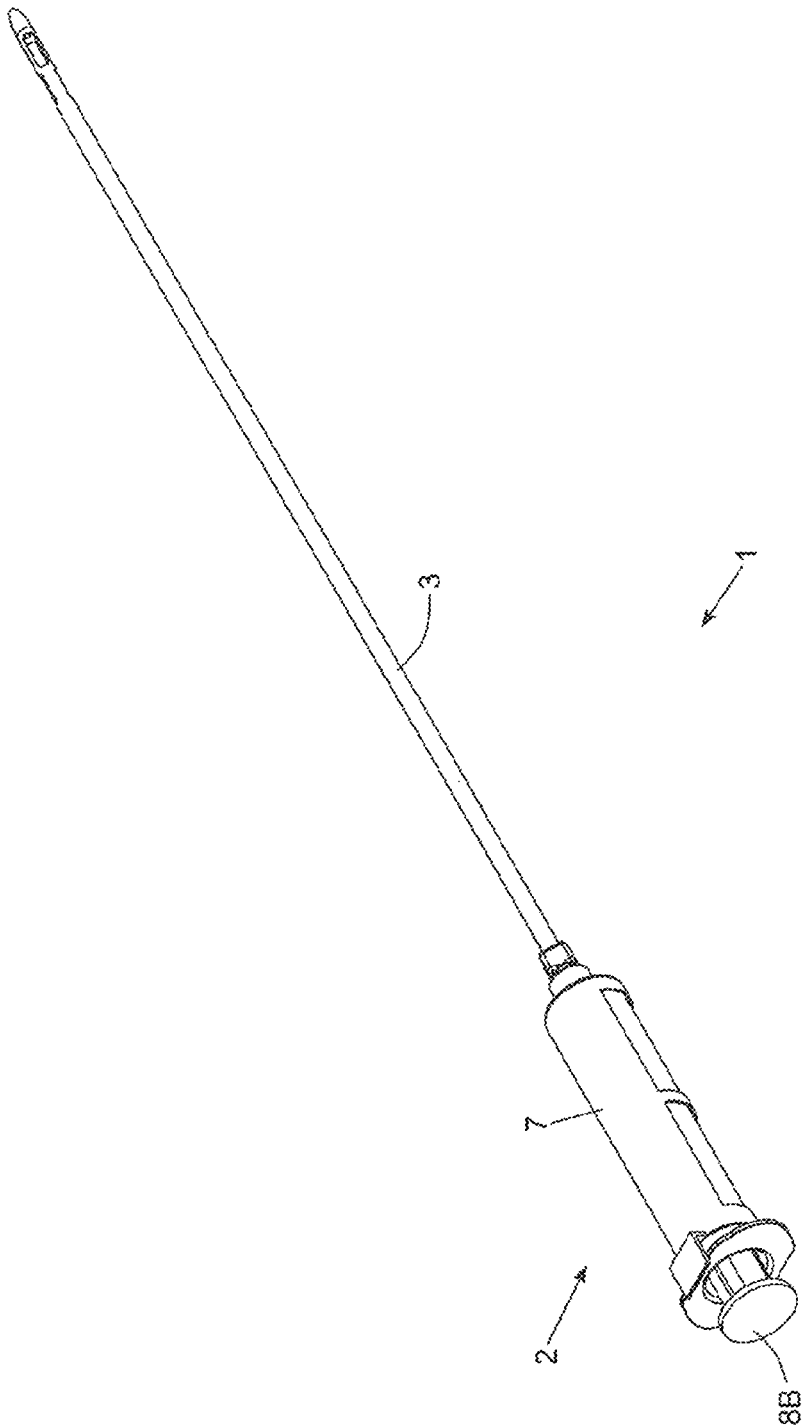
FIG. 15D is a perspective view of the tissue injection syringe device of FIG. 15D after it has been emptied of its tissue sample.

When all tissue has been emptied from the syringe device 2, it will be configured as shown in FIG. 15D.

Method of Harvesting, Processing and Injecting a Tissue Sample into a Patient Using the Tissue Sampling, Processing and Injection Syringe Device of the Present Invention The flow chart of FIG. 16 describes the primary steps carried out when practicing the method of harvesting, processing and injecting a tissue sample into a patient using the tissue sampling, processing and injection syringe device 2 of the present invention, depicted in FIGS. 13 through 15D. As these steps are a compilation of the steps previously described in the flow charts of FIGS. 13, 14 and 15, these steps will not be repeated here for sake of brevity.

Alternative Embodiments which Readily Come to Mind

While the tissue sampling, processing, collecting and re-injection devices of the illustrative embodiments of the present invention described above have been illustrated in connection with adipose (i.e. fat) tissue in the human body, it is understand that the methods and apparatus of the present invention can be used to sample, process, collection and re-inject other types of human tissue including, but not limited to, including autologous and allogeneic forms of musculoskeletal (i.e. bone, ligament, cartilage and skin) tissue, for use in autografting and allografting purposes.

Also, while it is preferred that the devices of the present invention be made from disposable, optically transparent, bio-compatible plastic materials, well known in the art, it is understood that such devices can be made from plastic and other types of materials that are not intended to be disposable, and capable of being processed using autoclaving and other sterilization processes known in the medical and surgical arts.

Several modifications to the illustrative embodiments have been described above. It is understood, however, that various other modifications to the illustrative embodiment of the present invention will readily occur to persons with ordinary skill in the art. All such modifications and variations are deemed to be within the scope and spirit of the present invention as defined by the accompanying Claims to Invention.

What is claimed is:

1. A tissue sampling, collection, and processing system comprising:
   a hand-supportable power-assisted tissue aspiration device having a cannula for aspirating fat tissue from a patient's body;
   a multi-pack tissue sampling, processing and collecting device containing multiple tissue collection tubes for collection of said aspirated fat tissue;
   a vacuum source operably connected to said multi-pack tissue sampling, processing and collecting device by a first section of vacuum tubing, and said multi-pack tissue sampling, processing and collecting device being operably connected to said hand-supportable power-assisted tissue aspiration device by a second section of vacuum tubing, so that said multi-pack tissue sampling, processing and collecting device is connected in-line between said vacuum source and said hand-supportable power-assisted tissue aspiration device; and
   wherein said multi-pack tissue sampling, processing and collecting device further includes a selector for selecting at least one of said multiple tissue collection tubes, into which a sample of aspirated fat tissue is directed to flow for collection and indexing purposes during tissue sampling; and
   wherein said at least one of said multiple tissue collection tubes is selectively filled with aspirated fat tissue during tissue aspiration operations performed by said hand-supportable power-assisted tissue aspiration device.

2. The tissue sampling, collection, and processing system of claim 1, wherein said multi-pack tissue sampling, processing and collecting device has a collection chamber containing said multiple tissue collection tubes, and wherein each said tissue collection tube has an interior volume disposed between a distal end opening and a proximal end opening, and micro-pores formed in said tissue collection tube between said distal and proximal end openings, and is supported on a suction mounting plate at said proximal end within said collection chamber, with a cap attached to the distal end opening of said distal tissue collection tube, and wherein said suction mounting plate has an opening connectable to said vacuum source.

3. The tissue sampling, collection, and processing system of claim 2, wherein said hand-supportable power-assisted tissue aspiration device is used to aspirate fat tissue samples from said patient's body, through said cannula, out of an outlet port provided on said hand-supportable power-assisted tissue aspiration device, and into one or more selected tissue collection tubes within said multi-pack tissue sampling, processing and collecting device so that as aspirated fat tissue is collected in said one or more said tissue collection tubes, fluid is permitted to express through said micro-pores during fat tissue harvesting operations; wherein after harvesting operations, said tissue collection tubes filled with aspirated fat tissue are removed from said collection chamber; and wherein said micro-pores on said tissue collection tube filled with aspirated fat tissue, are selectively occluded by snap-fitting a micro-pore occluder about said tissue collection tube and occluding said micro-pores therewith.

4. The tissue sampling, collection, and processing system of claim 3, wherein a plunger and piston assembly is partially inserted into said proximal end opening of each said tissue collection tube filled with aspirated fat tissue and having micro-pores occluded by said micro-pore occluder so as to form a tissue-filled injection syringe device.

5. The tissue sampling, collection, and processing system of claim 4, wherein said tissue-filled injection syringe device in placed in an autograft storage system.

6. The tissue sampling, collection, and processing system of claim 4, wherein said tissue-filled injection syringe device is used in autograft tissue re-injection procedures by simply removing said cap from the distal end opening of said tissue-filled injection syringe device and connecting a syringe cannula to said distal end opening via a Leur locking mechanism, and then inserting said syringe cannula within the body of a patient and pushing said plunger and piston assembly into the interior volume of said tissue collection tube.

7. The tissue sampling, collection, and processing system of claim 3, wherein filtered and concentrated cellular material contained within said tissue collection tube is subjected to further processing and cellular concentration, prior to being place in an autograft storage system; and thereafter, said tissue collection tube is removed from said autograft storage system and used in autograft tissue re-injection procedures.

8. A tissue sampling, collection, and processing system comprising:
   a power-assisted tissue aspiration device having a cannula for aspirating fat tissue from a patient's body;
   a multi-pack tissue sampling, processing and collecting device containing multiple tissue collection tubes for collection of said aspirated fat tissue;
   a vacuum source operably connected to said multi-pack tissue sampling, processing and collecting device by a first section of vacuum tubing, and said multi-pack tissue sampling, processing and collecting device being operably connected to said power-assisted tissue aspiration device by a second section of vacuum tubing, so that said multi-pack tissue sampling, processing and collecting device is connected in-line between said vacuum source and said power-assisted tissue aspiration device; and wherein said multi-pack tissue sampling, processing and collecting device further includes a selector for selecting at least one of said multiple tissue collection tubes, into which a sample of aspirated fat tissue is directed to flow for collection and indexing purposes during tissue sampling; and wherein said at least one of said multiple tissue collection tubes is selectively filled with aspirated fat tissue during tissue aspiration operations performed by said power-assisted tissue aspiration device.

9. The tissue sampling, collection, and processing system of claim 8, wherein said multi-pack tissue sampling, processing and collecting device has a collection chamber containing said multiple tissue collection tubes, and wherein each said tissue collection tube (i) has an interior volume disposed between a distal end opening and a proximal end opening, and micro-pores formed in said tissue collection tube between said distal and proximal end openings, and (ii) is supported on a suction mounting plate at said proximal end of said tissue collection tube, within said collection chamber, with a cap attached to the distal end opening of said tissue collection tube, and wherein said suction mounting plate is opening connectable to said vacuum source.

10. The tissue sampling, collection, and processing system of claim 9, wherein said power-assisted tissue aspiration device is used to aspirate fat tissue samples from said patient's body, through said cannula, out of an outlet port provided on said power-assisted tissue aspiration device, and into one or more selected tissue collection tubes within said multi-pack tissue sampling, processing and collecting device so that as fat tissue is collected in said one or more said tissue collection tubes, while fluid is permitted to express through said micro-pores during harvesting operations; wherein after harvesting operations, said tissue collection tubes filled with aspirated fat tissue are removed from said collection chamber; and wherein said micro-pores on said tissue collection tube filled with aspirated fat tissue, are selectively occluded by snap-fitting a micro-pore occluder about said tissue collection tube and occluding said micro-pores therewith.

11. The tissue sampling, collection, and processing system of claim 10, wherein a plunger and piston assembly is partially inserted into said proximal end opening of each said tissue collection tube filled with aspirated fat tissue and having micro-pores occluded by said micro-pore occluder so as to form a tissue-filled injection syringe device.

12. The tissue sampling, collection, and processing system of claim 11, wherein said tissue-filled injection syringe device in placed in an autograft storage system.

13. The tissue sampling, collection, and processing system of claim 11, wherein said tissue-filled injection syringe device is used in autograft tissue re-injection procedures by simply removing said cap from the distal end opening of said tissue-filled injection syringe device and connecting a syringe cannula to said distal end opening via a Leur locking mechanism, and then inserting said syringe cannula within the body of a patient and pushing said plunger and piston assembly into the interior volume of said tissue collection tube.

14. The tissue sampling, collection, and processing system of claim 10, wherein filtered and concentrated cellular material contained within said tissue collection tube is subjected to further processing and cellular concentration, prior to being place in an autograft storage system; and thereafter, said tissue collection tube is removed from said autograft storage system and used in autograft tissue re-injection procedures.

* * * * *